(12) United States Patent　　(10) Patent No.:　US 12,662,674 B2
Guo et al.　　(45) Date of Patent:　Jun. 23, 2026

(54) RNA NANOPARTICLE FOR LIVER CANCER TREATMENT

(71) Applicant: OHIO STATE INNOVATION FOUNDATION, Columbus, OH (US)

(72) Inventors: Peixuan Guo, Columbus, OH (US); Satheesh Ellipilli, Columbus, OH (US); Hongzhi Wang, Columbus, OH (US); Congcong Xu, Columbus, OH (US); Xin Li, Columbus, OH (US)

(73) Assignee: OHIO STATE INNOVATION FOUNDATION, Columbus, OH (US)

(*) Notice: Subject to any disclaimer, the term of this patent is extended or adjusted under 35 U.S.C. 154(b) by 971 days.

(21) Appl. No.: 17/757,303

(22) PCT Filed: Dec. 17, 2020

(86) PCT No.: PCT/US2020/065621
§ 371 (c)(1),
(2) Date: Jun. 14, 2022

(87) PCT Pub. No.: WO2021/127187
PCT Pub. Date: Jun. 24, 2021

(65) Prior Publication Data
US 2022/0372493 A1　　Nov. 24, 2022

Related U.S. Application Data

(60) Provisional application No. 62/951,717, filed on Dec. 20, 2019.

(51) Int. Cl.
*A61K 39/385*　　(2006.01)
*A61K 47/54*　　(2017.01)
(Continued)

(52) U.S. Cl.
CPC ........ *C12N 15/1138* (2013.01); *A61K 47/549* (2017.08); *A61K 47/6929* (2017.08);
(Continued)

(58) Field of Classification Search
None
See application file for complete search history.

(56) References Cited

U.S. PATENT DOCUMENTS 8,828,956 B2　9/2014　Manoharan et al.
2013/0183737 A1　7/2013　Borlak
(Continued)

FOREIGN PATENT DOCUMENTS

CN　　109568594 A　　4/2019
WO　　2016/028700 A1　　2/2016
(Continued)

OTHER PUBLICATIONS

EP Search Report, EP App. 20902636.8, mailed Dec. 21, 2023.
(Continued)

*Primary Examiner* — M Franco G Salvoza
(74) *Attorney, Agent, or Firm* — PABST PATENT GROUP LLP

(57)　　ABSTRACT

Disclosed herein are compositions and methods for targeted treatment of liver cancers with Paclitaxel and miR-122. The disclosed composition comprises RNA nanostructure conjugated to a hepatocyte targeting ligand, paclitaxel, and miR-122 for use in intracellular drug delivery to liver cancer cells. The RNA nanoparticle can involve three or more self-assembled synthetic RNA oligonucleotides that form a central core domain and at least three double-stranded arms arranged around the core domain and extending away from the central core domain.

11 Claims, 30 Drawing Sheets

(51) Int. Cl.

| | |
|---|---|
| *A61K 47/69* | (2017.01) |
| *A61P 35/00* | (2006.01) |
| *C12N 15/11* | (2006.01) |
| *C12N 15/113* | (2010.01) |
| *B82Y 5/00* | (2011.01) |

(52) U.S. Cl.
CPC ............ *A61P 35/00* (2018.01); *C12N 15/111* (2013.01); *B82Y 5/00* (2013.01); *C12N 2310/141* (2013.01); *C12N 2310/351* (2013.01); *C12N 2320/31* (2013.01); *C12N 2320/32* (2013.01)

(56) References Cited

U.S. PATENT DOCUMENTS

| | | | |
|---|---|---|---|
| 2016/0243248 A1 | 8/2016 | Hubbell et al. | |
| 2018/0369384 A1* | 12/2018 | Manoharan | ........... C07C 251/40 |
| 2019/0024085 A1 | 1/2019 | Guo et al. | |

FOREIGN PATENT DOCUMENTS

| | | | | |
|---|---|---|---|---|
| WO | WO-2017176894 A1 * | 10/2017 | ............... | A61K 9/51 |
| WO | 2017/197009 A1 | 11/2017 | | |
| WO | WO-2019156726 A1 * | 8/2019 | ............. | A61K 48/00 |

OTHER PUBLICATIONS

Wang, Hongzhi, et al., "Multivalent rubber-like RNA nanoparticles for targeted co-delivery of paclitaxel and MiRNA to silence the drug efflux transporter and liver cancer drug resistance," Journal of Controlled Release, vol. 330 (2021), pp. 173-184.

Varshosaz, Jaleh, et al., "Nanoparticles for targeted delivery of therapeutic and small interfering RNAs in hepatocellular carcinoma," World Journal of Gastroenterology, vol. 21 (2015), pp. 12022-12041.

Guo, Sijin, "RNA nanoparticle as a safe and effective drug delivery platform for cancer therapy," PhD Thesis, The Ohio State University, Dec. 12, 2019.

Shi, Liyu, et al., "The contribution of miR-122 to the innate immunity by regulating toll-like receptor 4 in hepatoma cells," BMC Gastroenterology, vol. 19 (2019) (9 pages).

Hsu, Shu-Hao, et al., "Cationic lipid nanoparticles for therapeutic delivery of siRNA and miRNA to murine liver tumor," Nanomedicine: Nanotechnology, Biology and Medicine, vol. 9 (2013), pp. 1169-1180.

Gao, Yu, et al., "Targeted Delivery of Paclitaxel in Liver Cancer Using Hyaluronic Acid Functionalized Mesoporous Hollow Alumina Nanoparticles," Hindawi BioMed Research International, vol. 2019 (10 pages).

Xu, Yanmin, et al., "MicroRNA-122 sensitizes HCC cancer cells to adriamycin and vincristine through modulating expression of MDR and inducing cell cycle arrest," Cancer Letters, vol. 310 (2011), pp. 160-169.

Yahya, Shaymaa M. M., et al., "Possible Role of microRNA-122 in Modulating Multidrug Resistance of Hepatocellular Carcinoma," In. J. Clin. Biochem, vol. 33 (2018), pp. 21-30.

Huesker, Matthes, et al., "Reversal of Drug Resistance of Hepatocellular Carcinoma Cells by Adenoviral Delivery of Anti-MDR1 Ribozymes," Hepatology, vol. 36, No. 4 (2002), pp. 874-884.

Fan, Yin-Ping, et al., "MiR-375 and Doxorubicin Co-delivered by Liposomes for Combination Therapy of Hepatocellular Carcinoma," Molecular Therapy: Nucleic Acids, vol. 7 (2017), pp. 181-195.

International Search Report and Written Opinion, PCT/US2020/65621, mailed Apr. 6, 2021 (9 pages).

Yang, Haitao, et al., "siRNA Targeting of MDR1 Reverses Multidrug Resistance in a Nude Mouse Model of Doxorubicin-resistant Human Hepatocellular Carcinoma," Anticancer Research, vol. 36 (2016), pp. 2675-2682.

Lou, Cong, et al., "Prodrug-nanoparticulate drug delivery strategies for cancer therapy," Review, vol. 35, Issue 11 (2014), pp. 556-566.

Wang, Hongzhi, et al., "Multivalent rubber-like RNA nanoparticles for targeted co-delivery of paclitaxel and MiRNA to silence the drug efflux transporter and liver cancer drug resistance," ScienceDirect, vol. 330 (2021), pp. 173-184.

Guo, Sijin, et al., "Ultra-thermostable RNA nanoparticles for solubilizing and high-yield loading of paclitaxel for breast cancer therapy," Nature Communications, vol. 11 (2020) (11 pages).

Needleman, Saul B., et al., "A General Method Applicable to the Search for Similarities in the Amino Acid Sequence of Two Proteins," Journal of Molecular Biology, vol. 48 (1970), pp. 443-453.

Choy, Cindy J., et al., "Tunable pH-Sensitive Linker for Controlled Release," Bioconjugate Chemical, vol. 27 (2016), pp. 824-830.

Schmaljohann, Dirk, "Thermo- and pH-responsive polymers in drug delivery," Advanced Drug Delivery Reviews, vol. 58 (2006), pp. 1655-1670.

Balamuralidhara, V., et al., "pH Sensitive Drug Delivery Systems: A Review," American Journal of Drug Discovery and Development, vol. 1 (2011), pp. 24-48.

Karimi, Mahdi, et al., "pH-Sensitive stimulus-responsive nanocarriers for targeted delivery of therapeutic agents," WIREs Nanomed Nanobiotechnology, vol. 8 (2016), pp. 696-716.

Patil, Rameshwar, et al., "Cellular Delivery of Doxorubicin via pH-Controlled Hydrazone Linkage Using Multifunctional Naon Vehicle Based on Boly(B-L-Malic Acid), International Journal of Molecular Science, vol. 13 (2012), pp. 11681-11693.

Masson, Christophe, et al., "pH-sensitive PEG lipids containing orthoester linkers: new potential tools for nonviral gene delivery," Journal of Controlled Release, vol. 99 (2004), pp. 423-434.

Masson, et al., Biomedical Nanomaterials, Ed. Zhao and Shen (2016) Antibody-Drug Conjugates (Xinyu Liu and Weiping Gao), Chapter 6.

* cited by examiner

Hepatocyte targeting ligands (1-{6-{4-(((2R,3R,4R,4R,5R,6R)-3-acetamido-4,5-dihydroxy-6-(hydroxymethyl)tetrahydro-2H-pyran-2-yl)oxy)butanamido)hexanoyl)-4-((tris(4-methoxyphenyl)methoxy)methyl)piperidin-4-yl)methyl (2-cyanoethyl) diisopropylphosphoramidite.

FIG. 2

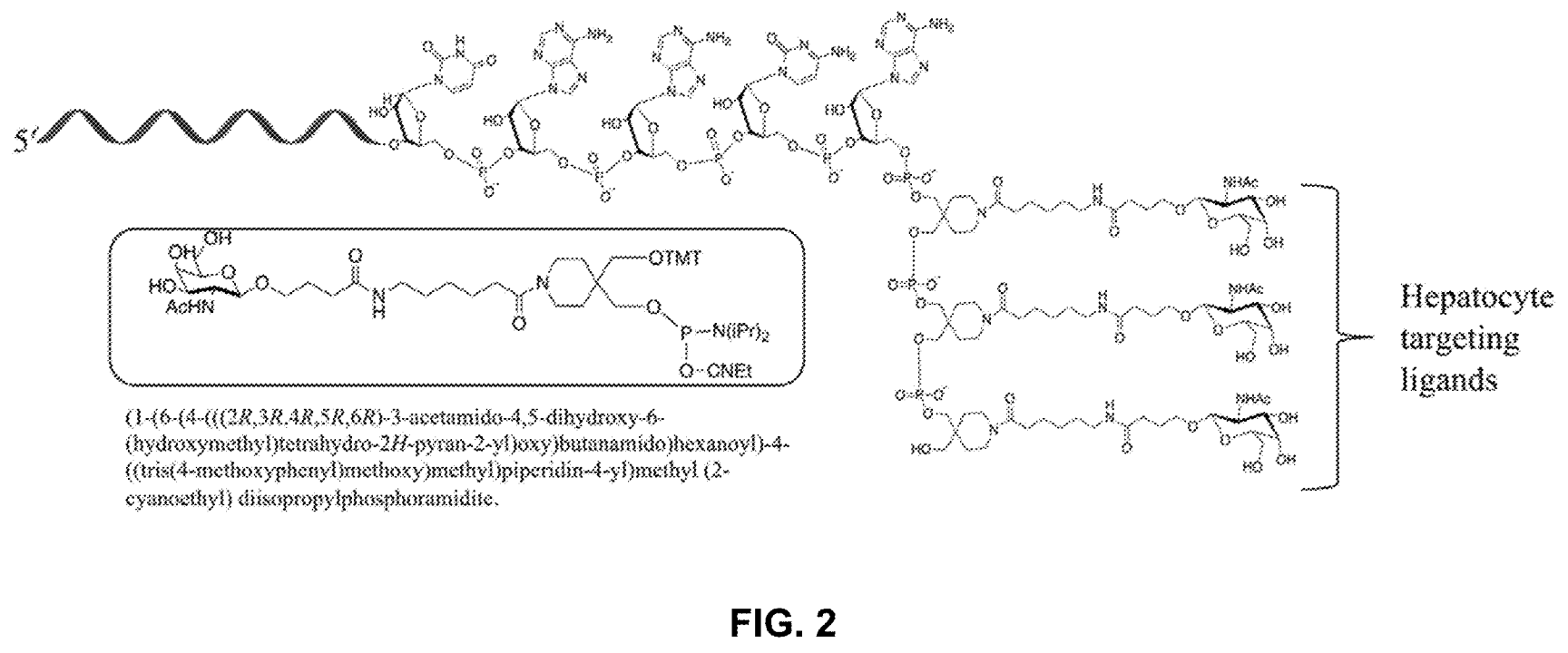

Monomer
Dimer
Trimer
Tetramer
Pentamer
RNA NP/PTX
RNA NP/PTX/HTL
RNA NP/PTX/HTL/miRNA-122

1. RNA 1
2. RNA 2
3. RNA 3
4. RNA 4
5. RNA 1/PTX
6. RNA 2/PTX
7. RNA 3/PTX
8. RNA 4/PTX

RNA NANOPARTICLE FOR LIVER CANCER TREATMENT

CROSS-REFERENCE TO RELATED APPLICATIONS

This application is a National Stage of International Application No. PCT/US2020/65621, filed Dec. 17, 2020, which claims benefit of U.S. Provisional Application No. 62/951,717, filed Dec. 20, 2019, which is hereby incorporated herein by reference in its entirety.

STATEMENT REGARDING FEDERALLY SPONSORED RESEARCH OR DEVELOPMENT

This invention was made with Government Support under Grant Nos. CA207946 and EB012135 awarded by the National Institutes of Health. The Government has certain rights in the invention.

BACKGROUND

Liver disease is one of the most common causes of millions of deaths worldwide and requires particular attention. The main challenge in realizing the full potential of cancer drugs is the efficient delivery of them to the targeted tumor sites without affecting healthy organs and tissues.

SUMMARY

Hepatocytes uniquely express asialoglycoprotein receptors (ASGP-R) on their sinusoidal surface. On the other hand, N-acetylgalactosamine with triantennary structure is a well-known hepatocyte targeted ligand due to its high affinity for (ASGP-R), overexpressed in hepatocytes (approximately 500,000 copies/cell). RNA nanoparticles were chosen for targeted drug delivery due to their tunable size, a long lifetime in the blood circulatory system, and the potential to conjugate various drugs and/or targeting ligands with a specified dose. Thus, it was hypothesized that RNA nanoparticles coupled with hepatocyte targeting ligands (HTLs) could efficiently deliver therapeutics to the liver disease site selectively. Disclosed herein is a combined drug delivery method using RNA nanoparticle (FIG. 3) scaffold with hepatocyte targeting ligands for liver cancer therapy. Paclitaxel (PTX) and microRNA-122 (miR-122) were chosen as therapeutic drugs for liver cancer therapy. Paclitaxel is a widely used cancer drug that binds to microtubule and leads to cell death by inactivating mitosis. Whereas, miR-122 acts as a liver cancer suppressor by targeting various hepatocarcinogenics such as ADAM10, IGF1R, SRF, and Wnt1. Thus, it was hypothesized that the RNA nanoparticle system with targeting ability could deliver the two cancer drugs (Paclitaxel and miR-122) to the hepatocyte cells with high affinity and specificity thus, potentially inhibit liver tumor growth as a result of their synergistic cytotoxic effect. Demonstrated herein are: i) Use of paclitaxel and micro RNA-122 for the treatment of liver cancer ii) Use of (1-(6-(4-(((2R,3R,4R,5R,6R)-3-acetamido-4,5-dihydroxy-6-(hydroxymethyl)tetrahydro-2H-pyran-2-yl)oxy)butanamido)hexanoyl)-4-((tris(4-methoxyphenyl)methoxy)methyl)piperidin-4-yl)methyl (2-cyanoethyl) diisopropylphosphoramidite as a building block in the construction RNA nanoparticle harboring hepatocyte targeting ligands to deliver drugs to hepatocyte cells with high affinity and specificity, iii) Construction of RNA nanoparticle as a carrier to deliver Paclitaxel and microRNA-122 with hepatocyte targeting ligand for the treatment of liver cancer. The proposed RNA nanoparticle formulation method to deliver combined therapeutic drugs with selectivity to liver cancer would be highly advantageous over non-targeted chemotherapy. The RNA nanoparticle formulation for liver cancer therapy is expected to outperform current treatment approaches in several aspects: (i) The RNA nanoparticles have defined size, structure, and stoichiometry, therefore, the unpredictable side effects arising from heterogeneous materials can be avoided. (ii) The RNA nanoparticle formulation anticipated delivering dual drugs to liver diseases with improved potency and specificity through receptor-mediated endocytosis. (iii) The synergistic cytotoxic effect of both Paclitaxel and miR-122 would result in higher toxicity, thus leading to the elimination of liver cancer or inhibition of cancer growth. Therefore, the proposed RNA nanoparticle formulation for various liver diseases would have higher therapeutic advantages over conventional chemotherapies.

Disclosed herein is a composition for treating hepatiocellular carcinoma (HCC) that involves an RNA nanostructure conjugated to a) one to three hepatocyte targeting ligand, b) a plurality of HCC therapeutic prodrugs, and c) a therapeutic oligonucleotide that suppresses or silences a drug efflux transporter.

In some embodiments, the therapeutic oligonucleotide is an siRNA against P-glycoproteins. In some embodiments, the therapeutic oligonucleotide is an miR122 oligonucleotide that can suppress the drug efflux function of P-glycoproteins.

In some embodiments, the hepatocyte targeting ligand comprises galactosamine molecules that bind asialoglycoprotein receptor (ASGP-R). In some embodiments, the hepatocyte targeting ligand can be selected from the group consisting of galactose, galactosamine, N-formyl-galactosamine, N-acetylgalactosamine, N-propionyl-galactosamine, N-n-butanoyl-galactosamine, and N-iso-butanoyl-galactos-amine. In some embodiments, the hepatocyte targeting ligand comprises a (1-(6-(4-(((2R,3R,4R,5R,6R)-3-acetamido-4,5-dihydroxy-6-(hydroxymethyl)tetrahydro-2H-pyran-2-yl)oxy)butanamido)hexanoyl)-4-((tris(4-methoxyphenyl)methoxy)methyl)piperidin-4-yl)methyl (2-cyanoethyl) diisopropylphosphoramidite molecule.

In some embodiments, the HCC therapeutic prodrug is a paclitaxel prodrug. In preferred embodiments, about 24 paclitaxel prodrug molecules are conjugated to the RNA nanoparticle. Therefore, in some embodiments, each RNA nanoparticle comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 paclitaxel prodrug molecules.

In some embodiments, the RNA nanoparticle comprises three to six self-assembled synthetic RNA oligonucleotides. The three to six synthetic RNA oligonucleotides can form a central core domain and at three to six double-stranded arms arranged around the core domain and extending away from the central core domain. Therefore, in some embodiments, the one to three hepatocyte targeting ligands are conjugated to a first double-stranded arm. In some embodiments, at least three heptatocyte targeting ligands are all conjugated to the first double-stranded arm. In some embodiments, a second double stranded arm comprises a sequence (e.g. single stranded) portion that is bound to the therapeutic oligonucleotide by complementary or partial complementary binding. In some embodiments, the HCC therapeutic prodrugs is conjugated to one or more of the double-stranded arms by click chemistry.

In particular, disclosed herein are compositions and methods for targeted treatment of liver cancers with Paclitaxel and miR-122. The disclosed composition comprises RNA nanostructure conjugated to a hepatocyte targeting ligand, paclitaxel, and miR-122 for use in intracellular drug delivery to liver cancer cells.

In some embodiments, the RNA nanostructures that can be composed of one or more synthetic RNA oligonucleotides that are designed (or configured) to self-assemble into the RNA nanostructure. When assembled, the RNA nanostructure can be composed of multiple double-stranded arms (DAs).

In some embodiments, at least one oligonucleotides of the RNA nanostructure are conjugated to the Paclitaxel. For example, alkyne RNA oligonucleotides can be reacted with Paclitaxel-azide via copper(I)-catalyzed alkyne-azide cycloaddition (CuAAC) reaction to produce Paclitaxel conjugated RNAs (RNA-PTX).

In some embodiments, the RNA nanostructures are designed according the methods of WO2016168784, which is incorporated by reference for the teaching of these RNA nanoparticles.

Also disclosed herein is a method of treating a liver cancer in a subject, comprising administering to the subject a therapeutically effective amount of the RNA nanoparticles disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a schematic diagram of synthesis of RNA strand harboring hepatocyte targeting galactosamine derivatives.

FIG. 6A shows TGGE of RNA/PTX nanoparticle. FIG. 6B shows TGGE of RNA/PTX/miR-122/HTL RNA nanoparticle. FIG. 6C shows quantification of Tm using ImageJ software. FIG. 6D shows Tm measurements using real-time PCR (All samples were completed in triplicate to ensure accuracy of the annealing temperatures and profiles).

FIG. 12A is a schematic representation of 6WJ/HTL/PTX/miR122 RNA nanoparticle. FIG. 12B shows conjugation of Paclitaxel-azide to RNA-alkyne using copper catalyzed click chemistry and assayed for purity by 16% urea PAGE gel. FIG. 12C shows HPLC profiles of 6WJ-6-alkyne and 6WJ-6-PTX RNA strands. FIG. 12D shows self-assembly of 6WJ/HTL, 6WJ/HTL/PTX and 6WJ/HTL/PTX/miR122 RNA nanoparticles, evaluated by 2% agarose gel.

FIG. 13A shows size comparison of 6WJ/HTL, 6WJ/HTL/PTX, and 6WJ/HTL/PTX/miR122 in aqueous solution by DLS (n=3, mean±SD). FIG. 13B shows thermal stability ($T_m$) of designed RNA nanoparticles (6WJ/HTL; 6WJ/HTL/PTX; and 6WJ/HTL/PTX/miR122) evaluated by 10% native TGGE (Temperature Gradient Gel Electrophoresis). FIG. 13C shows $T_m$ comparison of 6WJ/HTL, 6WJ/HTL/PTX, and 6WJ/HTL/PTX/miR122 by thermal cycler (n=3).

FIG. 14A shows results of a binding assay of 6WJ/HTL & 6WJ/HTL/PTX/miR122 nanoparticles to ASGP-R positive HepG2 cells and ASGP-R negative KB cells as negative control. FIG. 14B shows effect of concentration on binding affinity of 6WJ and 6WJ/HTL nanoparticles to ASGP-R positive HepG2 cells. FIG. 14C shows results of a competitive assay of free galactosamine with 6WJ/HTL and 6WJ nanoparticle against ASGP-R positive HepG2, respectively. FIG. 14D shows confocal imaging showing the internalization of 6WJ and 6WJ/HTL/PTX/miR122 nanoparticles into HepG2 cells, nuclei, cytoskeleton and RNA nanoparticles, 100 μm for original images, and 20 μm for magnified images.

FIG. 15A shows qRT-PCR showing effect of miR122 knockdown on ADAM 10 gene expression. FIG. 15B is a Western blot showing the knock-down of ADAM10 and MDR1 proteins expression. FIG. 15C shows quantification of ADAM10 & MDR1 proteins expression from western blot. (n=3 biologically independent animals, statistics was calculated by two-tailed unpaired t-test presented as mean±SD, *p<0.05, p<0.01, **p<0.0001).

FIG. 16A shows PTX release from single stranded RNA at 50% fetal bovine serum characterized by 16% urea PAGE gel. FIG. 16B shows LC/MS quantification of PTX release from assembled 6WJ/HTL/PTX/miR122 nanoparticles at 50% fetal bovine serum.

FIG. 17A shows results of an MTT assay (n=3; mean±SD). FIG. 17B shows results of a caspase-3 assay.

FIG. 18A shows quantitative analysis of RNA nanoparticle biodistribution in tumors and normal organs. FIG. 18B shows liver cancer tumors harvested from mice after treatments. FIG. 18C shows intravenous treatment of nude mice bearing HepG2 xenografts with 6WJ/HTL/PTX/miR122 and control groups treated every three days for a total of 7 injections. Tumor size was monitored during the treatments (n=5 biologically independent animals, statistics was calculated by two-tailed unpaired t-test presented as mean±SD, $*p<0.05$, $p<0.01$, $**p<0.0001$).

FIG. 19 shows in vivo immune-toxicity assay of 6WJ/HTL/PTX/miR122 nanoparticles. Evaluation of TNF-$\alpha$, IL-6, IL-12, and IFN-$\gamma$ secretion in mice after systemic injection of 6WJ/HTL/PTX/miR122 nanoparticles, evaluated by ELISA (n=3; mean±SD).

DETAILED DESCRIPTION

Figure 1:
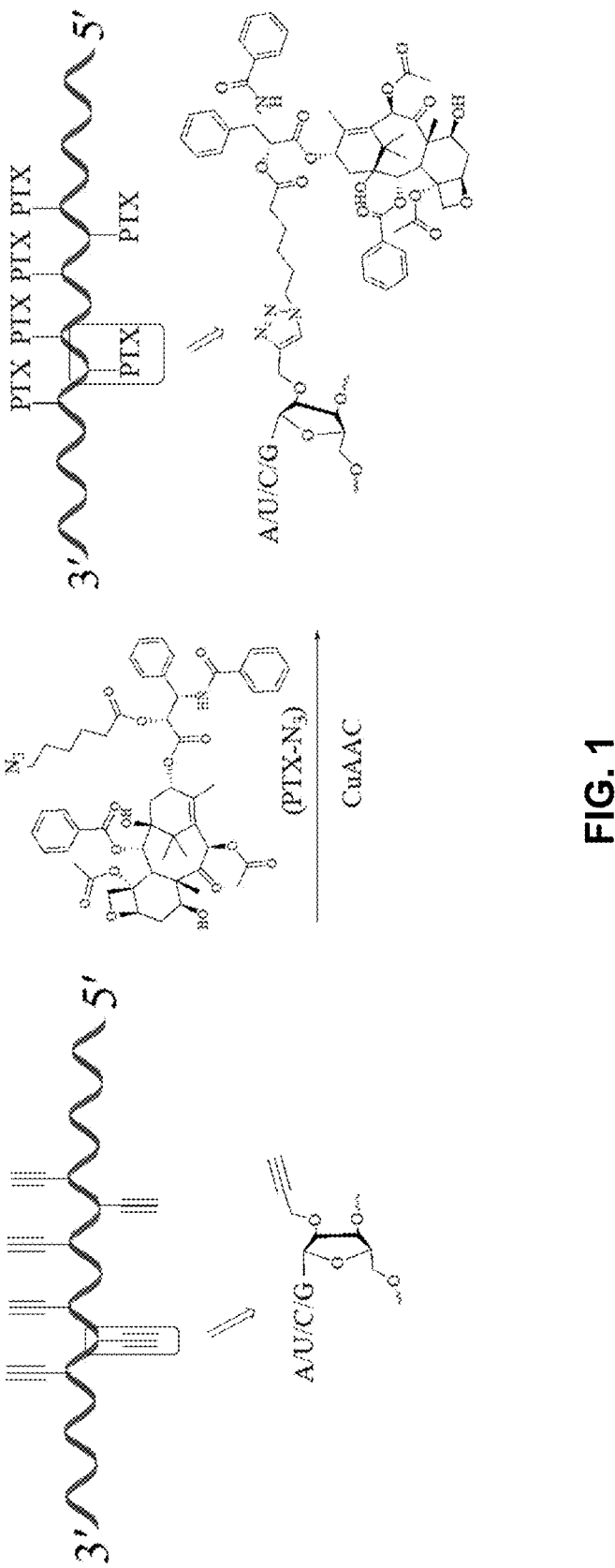
FIG. 1 is a schematic representation of Paclitaxel conjugation to RNA-alkyne strands using CuAAC reaction.
Figure 3:
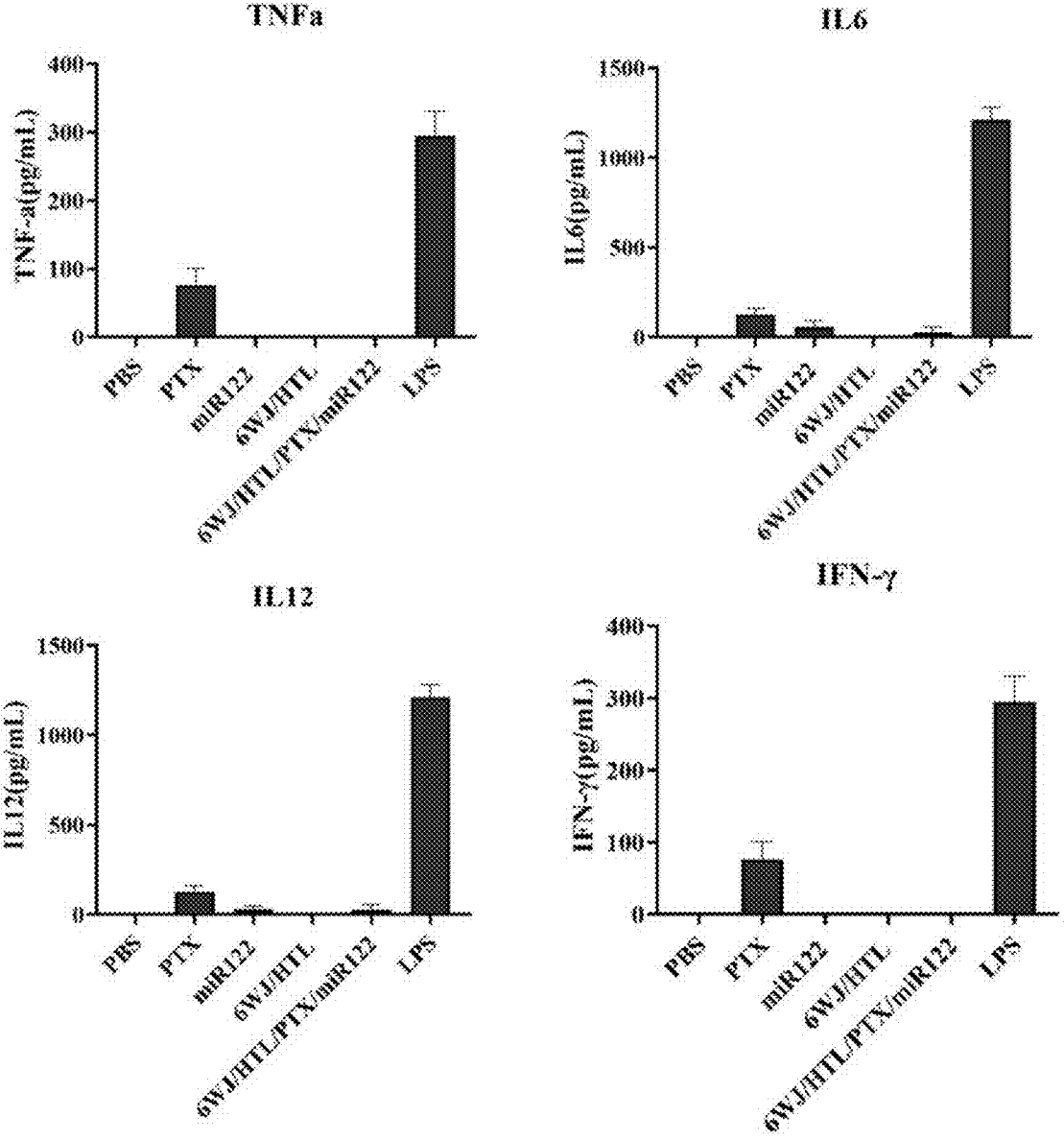
FIG. 3 shows $^1$H-NMR spectrum of Paclitaxel-azide
Figure 4:
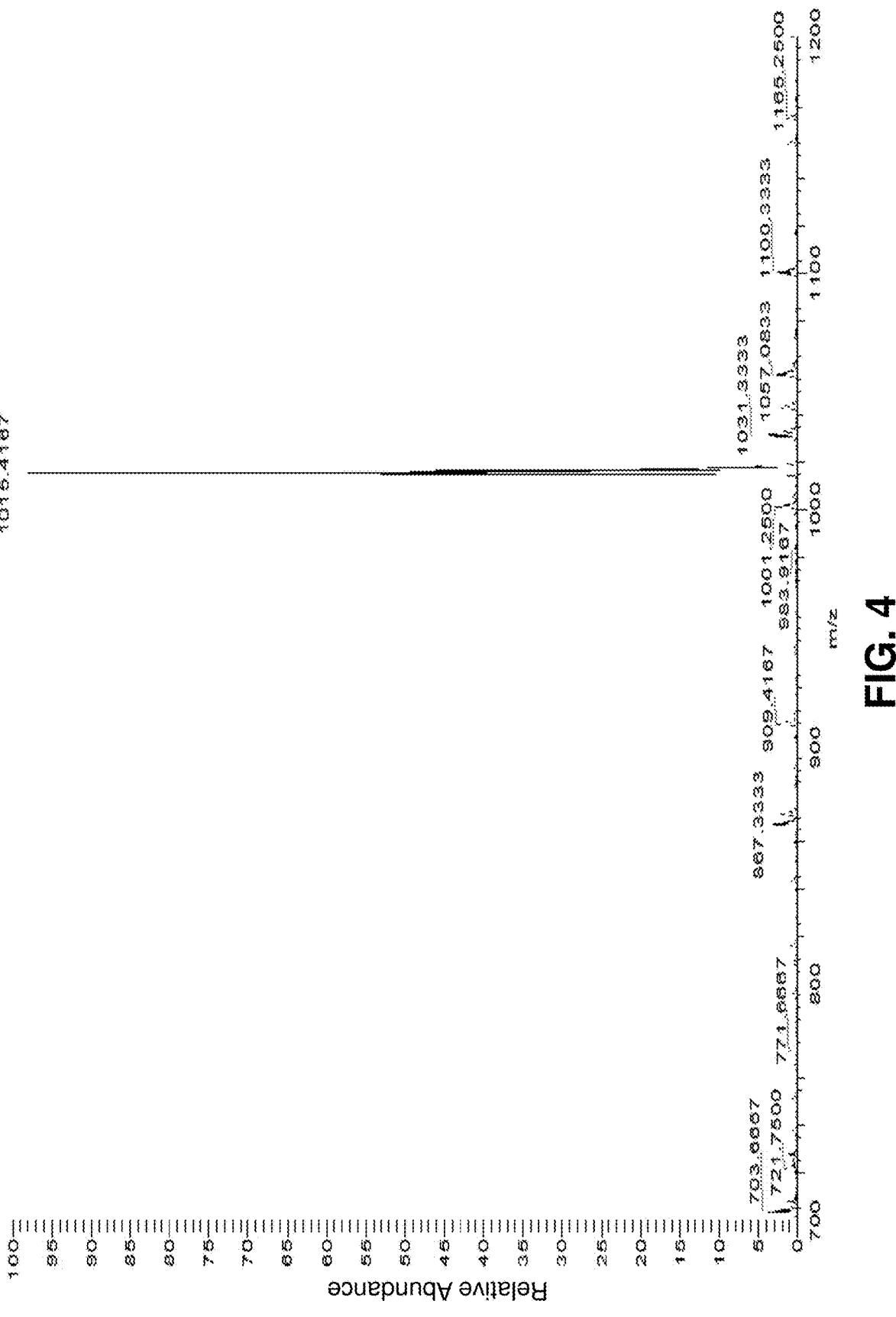
FIG. 4 shows mass spectrum of Paclitaxel-azide: calculated mass for $C_{53}H_{60}N_4NaO_{15}$ [M+Na]$^+$ is 1015.3953, observed mass is 1015.4167.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, "active agent" or "active ingredient" refers to a component or components of a composition to which the whole or part of the effect of the composition is attributed. Active agents can be pharmaceutically active compounds, molecules (including but not limited to chemical and biological molecules), or other substance that, when in contact with an RNA nanostructure and/or when not in contact with an RNA nanostructure can elicit an effect (e.g. a pharmaceutical and/or biological effect) in a subject to which it is administered.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein "anti-infectives" can include, but are not limited to, antibiotics, antibacterials, antifungals, antivirals, and antiproatozoals.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, "control" is an alternative subject or sample used in an experiment for comparison purposes and included to minimize or distinguish the effect of variables other than an independent variable. A "control" can be positive or negative.

As used herein, "coupled" or "coupled to" refers to the direct or indirect attachment or linkage or other joining of two or more components of a larger structure or system.

As used herein, "conjugated" has the same meaning as "attached".

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

As used herein, "identity," "identical to", and the like can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, the term "motif" in reference to a nanparticle age is meant to refer to a double-stranded or single-stranded ribonucleic acid or analog thereof. Individual motifs are joined together into larger particles by attachment to each other. Attachment can occur by non-covalent linking.

As used herein, the term "nanoparticle" is meant to refer to a particle between 1 nm up to 1,000 nm in dimeter. The nanoparticle can be between 5 nm and 30, 10 nm and 50 nm, between 10 nm and 40 nm, between 10 nm and 30 nm, between 10 nm and 20 nm, and 10 nm and 15 nm. The RNA can be obtained from any source, for example bacteriophages phi 29, HIV, Drosophila, the ribosome, or be a synthetic RNA.

As used herein, the term "nanostructure" is meant to refer to a structure between 1 nm up to 1,000 nm when measured along its largest dimension in any direction. The nanostructure can be between 5 nm and 30, 10 nm and 50 nm, between 10 nm and 40 nm, between 10 nm and 30 nm, between 10 nm, and 20 nm, and 10 nm and 15 nm as measured along its largest dimension in any direction.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. In particular, "Polynucleotide" and "nucleic acids" also includes 2' Fluoro, 2'O-methyl, LNA (locked nucleic acids), and other variants of 2' modifications of the ribose (sugar) moiety of native nucleic acids. Natural nucleic acids have a proton or hydroxyl group at the 2'ribose position (DNA and RNA, respectively), artificial nucleic acids may contain other types of 2' modification to increase thermodynamic and enzymatic stability. Thus, DNAs or RNAs with the 2' ribose position modified for stability or for other reasons are "nucleic acids" or "polynucleotide" as that term is intended herein. As used herein, "nucleic acid sequence" and "oligonucleotide" also encompasses a nucleic acid and polynucleotide as defined above.

The term "pharmaceutically acceptable" describes a material that is not biologically or otherwise undesirable, i.e., without causing an unacceptable level of undesirable biological effects or interacting in a deleterious manner.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. In some aspects, at least 95% by weight of the particles of the active ingredient have an effective particle size in the range of 0.01 to 10 micrometers.

As used herein, the term "prevent" or "preventing" refers to precluding, averting, obviating, forestalling, stopping, or hindering something, e.g. a disease or symptom thereof, from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells. The term "prevent" or "preventing" includes maintaining or limiting a disease in a subclinical state.

As used herein, "self-assembly" refers to the ability of nucleic acids (and, in some instances, preformed nucleic acid nanostructures (e.g., crystals)) to anneal to each other, in a sequence-specific manner, in a predicted manner and without external control. In some aspects, nucleic acid nanostructure self-assembly methods include combining nucleic acids (e.g., single-stranded nucleic acids, or oligonucleotides) in a single vessel and allowing the nucleic acids to anneal to each other, based on sequence complementarity. In some aspects, this annealing process involves placing the nucleic acids at an elevated temperature and then reducing the temperature gradually in order to favor sequence-specific binding. Various nucleic acid nanostructures or self-assembly methods are known and described herein.

As used herein, the term "subject" refers to the target of administration, e.g., an animal, human, cell, or population of cells. Thus, the subject of the herein disclosed methods can be a vertebrate, such as a mammal, a fish, a bird, a reptile, or an amphibian. The subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

RNA Nanostructures

Described herein are RNA nanostructures that can be composed of one or more synthetic RNA oligonucleotides that are designed (or configured) to self-assemble into the RNA nanostructure. When assembled, the RNA nanostructure can be composed of multiple double-stranded arms (DAs).

The RNA nanostructure can be composed of 3, 4, 5, 6, 7, 8, or 9 synthetic single-stranded RNA oligonucleotides that can self-assemble into the RNA nanostructure via hybridization. Each synthetic single-stranded RNA oligonucleotide can be about 16 to about 120 bases in length. The exact sequence of each synthetic single-stranded RNA oligonucleotide in each RNA nanostructure can be designed such that they achieve specific physical characteristics when assembled with 2 or more other synthetic single-stranded RNA oligonucleotides. The 2-D structure can depend, at least in part, on the number of synthetic RNA oligonucleotides. The RNA nanostructures can have 3, 4, 5, 6, 7, 8, or 9 double-stranded arms (DAs). The DAs can be symmetrically or asymmetrically arranged.

Synthetic RNA Oligonucleotides

The synthetic RNA oligonucleotides can be single-stranded. Each individual synthetic RNA oligonucleotide can be composed of 16-120 nucleotides. The nucleotides can be native ribonucleotide or can be modified. In some aspects, the synthetic RNA oligonucleotide(s) can be 2' modified. The 2' or other modification can be a 2'Fluoro-, 2'O-methyl-, LNA- or any other backbone, sugar, or base modified ribonucleotide or any combination of native, backbone, sugar, and base modified ribonucleotides. Modifications are further discussed elsewhere herein. Each synthetic RNA oligonucleotide can be composed of 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides or any range therein. Each synthetic RNA oligonucleotide can be designed and configured such that it can self-assemble with 2, 3, 4, 5, 6, 7, or 8 other synthetic RNA oligonucleotides into a modular RNA motif as described elsewhere herein.

The nucleotides can be unmodified or modified nucleotides. The modifications can be 5'-terminal modifications and/or 3'-terminal modifications and/or 2'-internal sugar modifications and/or base-internal modifications. Typical 5' terminal modifications include amino, carboxy, phosphate, thiol, maleimide, alkyne, cholesterol, aldehyde, carbon spacers, Peg-spacer, doubler, trebler, photocleavable amino, photocleavable spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 5' modifications known to an experienced user of the art. Typical 3' terminal modifications include amino, carboxy, phosphate, thiol, alkyne, cholesterol, carbon spacers, Peg-spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 3' modifications known to an experienced user of the art. Typical internal modifications include amino-dA, amino-dC, amino-dT, carboxy-dT, 2'O-propargyl, 2'amino, 2'fluoro, 2'methoxy, 5-ethynyl-dU, C8-alkyne-dC, C8-alkyne-dT, carbon spacers, Peg-spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 5' modifications known to an experienced user of the art. The modification can be an alkyne group attached to a nucleotide. The modification can be a functional group attached to a nucleotide, such as the functional groups disclosed herein.

The alkyne group(s) or functional group(s) present in each synthetic RNA oligonucleotide can facilitate conjugation of a cargo compound at the site(s) containing the alkyne group via, for example, click chemistry. One or more of the terminal (e.g. the 5' and/or 3' end) nucleotides can be modified in a synthetic RNA oligonucleotide. One or both termini of the synthetic RNA oligonucleotide can be modified. In some aspects, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides can be modified. In some aspects, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides can be unmodified. If considering each nucleotide in a synthetic RNA oligonucleotide sequentially from the 5' terminal to the 3' terminal ends, the modified nucleotide(s) can be nucleotide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 or any combination thereof. Where more than one modified nucleotide is present, the modified nucleotides can be next to each other or can be spaced apart by one or more unmodified nucleotides. In some aspects, 1, 2, 3, 4, 5, 6, 7, 8, 9, 10 or more unmodified nucleotides can be between two modified nucleotides.

Methods of Making the Synthetic RNA Oligonucleotides

The synthetic RNA oligonucleotides, polynucleotide functional groups, and polynucleotide cargo compounds can be synthesized using standard molecular biologic and biochemical techniques. In other words, the various nucleic acids that can form the RNA nanoparticles can be de novo synthesized as desired or be generated from various nucleic acid expression vectors or transcribed in vitro. Such synthesis techniques will be known to the skilled artisan.

In some aspects, the linker can be a pH responsive linker. pH responsive linkers can be any compound that can degrade (e.g. hydrolyze) at a certain pH. Thus the pH responsive linkers can be acidic responsive or basic responsive. The pH responsive linkers can be polymers. Suitable pH responsive linkers are generally known in the art and include, but are not limited to those described in Choy et al. (Bioconjugate. Chem. (2016) 27:824-830; Schmaljohann (2008) Adv. Drug Deliv. Rev. (2006) 58:1655-1670, Balamuralidhara et al. (2011) Am. J. Drug Disc. Devel. 1:24-48; Biomedical Nanomaterials, ed. Zhao and Shen (2016), Chapter 6; Masson et al. (2004) J. Control Release. 99:423-434; Karimi et al., Nanomed. and Nanobiotech. (2016) 8:696-716; International Patent Application Publication No.: WO2016/028700; and Patil et al., 2012. Int. J. Mol. Sci. 13:11681-11693.

In some aspects, the linker can be an enzyme cleavable linker. Enzyme cleavable linkers are those that contain a cleavage site for an enzyme. In some aspects the linkers can be a nucleic acid that contains a sequences for an endonuclease. Endonuclease cleavage sites and how to produce nucleic acid molecules containing them will be appreciated by those of ordinary skill in the art. Other cleavage sites that can be contained can be RNAse or DNAse cleavage sites. In some aspects, the enzyme cleavage site can be a cleavage site for an enzyme that is specific to a target cell. Thus in this way, release can be controlled such that it occurs only at the target cell via interaction with the target-cell specific enzyme. In some aspects the linkers can be a chemical group that can be cleaved or hydrolyzed by an enzyme such as an esterase. Other cleavage sites that can be incorporated into the enzyme cleavable linkers will be instantly appreciated by those of skill in the art.

RNA Nanostructure Formulations

Also provided herein are pharmaceutical formulations that can include an amount of an RNA nanostructure described herein and a pharmaceutical carrier appropriate for administration to an individual in need thereof. The individual in need thereof can have or can be suspected of a cancer. The pharmaceutical formulations can include an amount of an RNA nanostructure described herein that can be effective to treat or prevent a cancer.

Formulations can be administered via any suitable administration route. For example, the formulations (and/or compositions) can be administered to the subject in need thereof orally, intravenously, occularly, intraoccularly, intramuscularly, intravaginally, intraperitoneally, rectally, parenterally, topically, intranasally, or subcutaneously. Other suitable routes are described herein. In some aspects, the RNA nanostructure contains an effective amount of a cargo molecule.

The RNA nanostructure can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the RNA nanostructures as described herein can be prepared in water or another solvent or dispersing medium suitably mixed with one or more pharmaceutically acceptable excipients including, but not limited to, surfactants, dispersants, emulsifiers, pH modifying agents, and combinations thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the RNA nanostructures.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the RNA nanostructures in the required amount in the appropriate solvent or dispersion medium with one or more of the excipients listed above, as required, followed by filtered sterilization. Dispersions can be prepared by incorporating the various sterilized RNA nanostructures into a sterile vehicle which contains the basic dispersion medium and the required other ingredients from those listed above. Sterile powders for the preparation of sterile injectable solutions can be prepared by vacuum-drying and freeze-drying techniques, which yields a powder of the RNA nanostructures plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more RNA nanostructures. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other aspects, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for use of nanotechnology including nanoformulations for parenteral administration can also contain one or more excipients, such as dispersing agents, wetting agents, and suspending agents.

The RNA nanostructures as described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations containing RNA nanostructures as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing an RNA nanostructure as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing an RNA nanostructure as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing an RNA nanostructure as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

In some aspects, an amount of one or more additional active agents are included in the pharmaceutical formulation containing an RNA nanostructure. Suitable additional active agents include, but are not limited to, DNA, RNA, modified ribonucleotides, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable additional active agents include, sensitizers (such as radiosensitizers). The RNA nanostructure can be used as a monotherapy or in combination with other active agents for treatment or prevention of a disease or disorder.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN- κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, nonsteroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H$_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H$_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein.

Methods of Using the RNA Nanostructures and Formulations Thereof

The RNA nanostructure as provided herein can be administered to a subject in need thereof, cell, or population thereof. The subject in need thereof can have a liver cancer. The amount delivered can be an effective amount of an RNA nanostructure provided herein. The subject in need thereof can be symptomatic or asymptomatic. In some aspects, the RNA nanostructures provided herein can be co-administered with another active agent. It will be appreciated that co-administered can refer to an additional compound that is included in the formulation or provided in a dosage form separate from the RNA nanostructure or formulation thereof. The effective amount of the RNA nanostructure or formulation thereof, such as those described herein, can range from about 0.1 mg/kg to about 500 mg/kg. In some aspects, the effective amount ranges from about 0.1 mg/kg to 10 mg/kg. In additional aspects, the effective amount ranges from about 0.1 mg/kg to 100 mg/kg. If further aspects, the effective amount ranges from about 0.1 mg to about 1000 mg. In some aspects, the effective amount can be about 500 mg to about 1000 mg.

Administration of the RNA nanostructures and formulations thereof can be systemic or localized. The compounds and formulations described herein can be administered to the subject in need thereof one or more times per day. In an aspect, the compound(s) and/or formulation(s) thereof can be administered once daily. In some aspects, the compound(s) and/or formulation(s) thereof can be administered given once daily. In another aspect, the compound(s) and/or formulation(s) thereof can be administered twice daily. In some aspects, when administered, an effective amount of the compounds and/or formulations are administered to the subject in need thereof. The compound(s) and/or formulation(s) thereof can be administered one or more times per week. In some aspects the compound(s) and/or formulation(s) thereof can be administered 1 day per week. In other aspects, the compound(s) and/or formulation(s) thereof can be administered 2 to 7 days per week.

In some aspects, the RNA nanostructure(s) and/or formulation(s) thereof, can be administered in a dosage form. The amount or effective amount of the compound(s) and/or formulation(s) thereof can be divided into multiple dosage forms. For example, the effective amount can be split into two dosage forms and the first dosage form can be administered, for example, in the morning, and the second dosage form can be administered in the evening. Although the effective amount is given over two doses, in one day, the subject receives the effective amount. In some aspects the effective amount is about 0.1 to about 1000 mg per day. The effective amount in a dosage form can range from about 0.1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

The RNA nanostructures described herein can be used in the preparation of a medicament for treatment of a disease or a cancer.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Use of RNA Nanoparticles Harboring Paclitaxel, miR-122, and Three Parallel 4-(((2R,3R, 4R,5R,6R)-3-acetamido-4,5-dihydroxy-6-(hydroxymethyl)tetrahydro-2H-pyran-2-yl)oxy)-N-(6-(4,4-bis(hydroxymethyl)piperidin-1-yl)-6-oxohexyl) butanamide to Target Hepatocyte for the Treatment of Liver Cancer An RNA nanotechnology approach was adopted to deliver multiple drugs due to their superior properties as nanoparticle. The RNA nanoparticles are biodegradable, non-immunogenic with tunable size and shape. Moreover, they exhibit high bioavailability, and facilitate high drug loading and targeting ligands. The RNA nanoparticles were modified with 2'Fluoro uracil and cytosine in order to improve their chemical, enzymatic, and thermal stability. Here, RNA nanoparticles were constructed harboring 24 copies of paclitaxel, one copy of miR-122, and 3 copies of hepatocyte targeting ligands.

Paclitaxel (PTX) is one of the widely used chemotherapeutic drugs for various cancer types, and its chemotherapeutic function comes from microtubules binding followed by G2 or M phase of the cell cycle arrest that ultimately leads to cell death. However, paclitaxel treatment for cancer showed adverse side effects due to its low water solubility, poor cell permeability and its nonspecific accumulation in various healthy organs. However, conjugation of Paclitaxel to RNA nanoparticles as a prodrug showed improved solubility and cell permeability. The paclitaxel conjugated RNA strands were synthesized by conjugating paclitaxel-azide to RNA-alkyne strands using copper catalyzed click chemistry as shown in FIG. 1.

MicroRNAs are short non-coding RNAs that regulate and maintain a broad spectrum of genes. Particularly, microRNA-122 regulates hepatocyte development, differentiation, homeostasis, and lipid metabolism by regulating a set of genes, however, loss of the miR-122 compromises hepatocyte functions and promotes hepatocarcinogenesis. Moreover, several reports suggest that miR-122 can act as a potential therapeutic agent for the treatment of various liver diseases, particularly hepatocellular carcinoma (HCC) by binding to various genes involved in HCC development. Therefore, the miR-122 sequence was included in RNA nanoparticle by extending one of the RNA strands used for the construction of nanoparticle with micro RNA-122 sequence.

The asialoglycoprotein receptor (ASGP-R) are highly over expressed on hepatocyte cells and are selective to various glycoproteins. N-acetylgalactosamine is one of the mostly used hepatocyte targeting ligand to target ASGP receptors. However, the distance between the receptor and the targeting ligand should be optimal in order to obtain maximum binding affinity. Here three 4-(((2R,3R,4R,5R, 6R)-3-acetamido-4,5-dihydroxy-6-(hydroxymethyl)tetrahydro-2H-pyran-2-yl)oxy)-N-(6-(4,4-bis(hydroxymethyl) piperidin-1-yl)-6-oxohexyl)butanamide molecules were incorporated parallelly during the synthesis an RNA (FIG. 2) that used for the construction of RNA nanoparticle. The RNA nanoparticle harboring three hepatocyte targeting ligands showed high binding affinity towards ASGPR expressing cells.

Thus, an RNA nanoparticle harboring Paclitaxel, miR-122 and hepatocyte targeting ligands together could efficiently deliver drugs to hepatocytes and reduce tumor growth in xenograft mouse model.

The commercially available paclitaxel was modified to Paclitaxel-azide, a facile functional handle to conjugate paclitaxel to RNA-alkyne through copper-mediated click chemistry. Paclitaxel-azide synthesis: To a solution of 6-azidohexanoicacid in dichloromethane, DCC, and DMAP were added and stirred for 15.0 min, to the above solution Paclitaxel pre-dissolved in DCM was added and stirred the reaction mixture at room temperature for 12 h. After completion of the reaction, the reaction mixture was concentrated. The product was extracted to ethyl acetate over water using the phase separation method. The organic layer was dried over anhydrous sodium carbonate and concentrated. The paclitaxel-azide purified using silica gel column chromatography.

$^1$H NMR (400 MHz, CDCl$_3$) δ (ppm): 1.2 (s, 3H), 1.4 (m, 2H), 1.5-1.7 (m, 6H), 1.8 (s, 3H), 1.9 (m, 1H), 2.0 (s, 3H), 2.1 (s, 3H), 2.2 (m, 1H), 2.3 (s, 3H), 2.4 (m, 3H), 2.5 (s, 3H), 2.6 (m, 2H), 3.2 (t, 2H), 3.9 (d, 1H), 4.2 (d, 1H), 4.4 (d, 1H), 4.5 (m, 1H), 5.0 (d, 1H), 5.5 (s, 1H), 6.0 (dd, 1H), 6.3 (m, 2H), 6.9 (d, 1H), 7.4 (m, 7H), 7.5 (m, 3H), 7.6 (t, 1H), 7.8 (d, 2H), 8.2 (d, 2H); LC-MS (ESI-TOF): m/z calculated for $C_{53}H_{60}N_4NaO_{15}$ [M+Na]$^+$ is 1015.3953, found is 1015.4167.

Figure 5B:
FIG. 5B shows RNA nanoparticle assembly using bottom-up self-assembly approach.
Figure 5B:
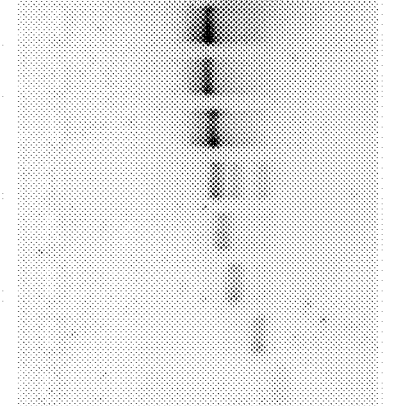
Figure 5A:
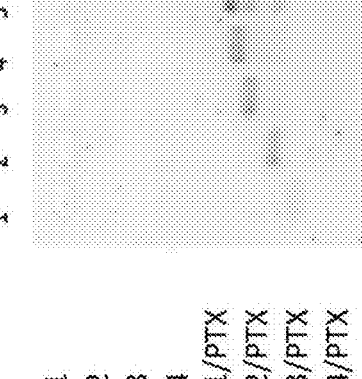
FIG. 5A shows conjugation of Paclitaxel-azide to Alkyne-RNAs using copper(I)-catalyzed alkyne-azide cycloaddition click chemistry and assayed by 16% TBE PAGE.
Figure 5A:
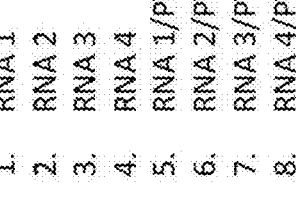
Figure 5A:
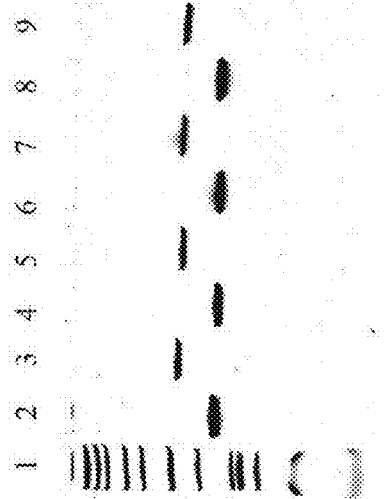

The alkyne RNA strands were reacted with Paclitaxel-azide via copper(I)-catalyzed alkyne-azide cycloaddition (CuAAC) reaction to produce Paclitaxel conjugated RNAs (RNA-PTX) with high efficiency. The successful conjugation was revealed by the slower migration of RNA-PTX strands in 16% 8M Urea PAGE due to increased molecular weight from six Paclitaxel molecules (FIG. 5A). By conjugating Paclitaxel to RNA, the poor water-solubility of Paclitaxel was significantly improved as the RNA/PTX can be well-dissolved in saline solution after conjugation.

The RNA nanoparticle constructed using a bottom-up self-assembly approach to obtain RNA nanoparticle harboring PTX, miR-122, and hepatocyte targeting ligand ligands. The successful assembly was assessed using 2% (w/v) agarose gel in TAE buffer and compared the RNA-nanoparticle assembly to their control nanoparticle assemblies (FIG. 5B).

Figure 6B:
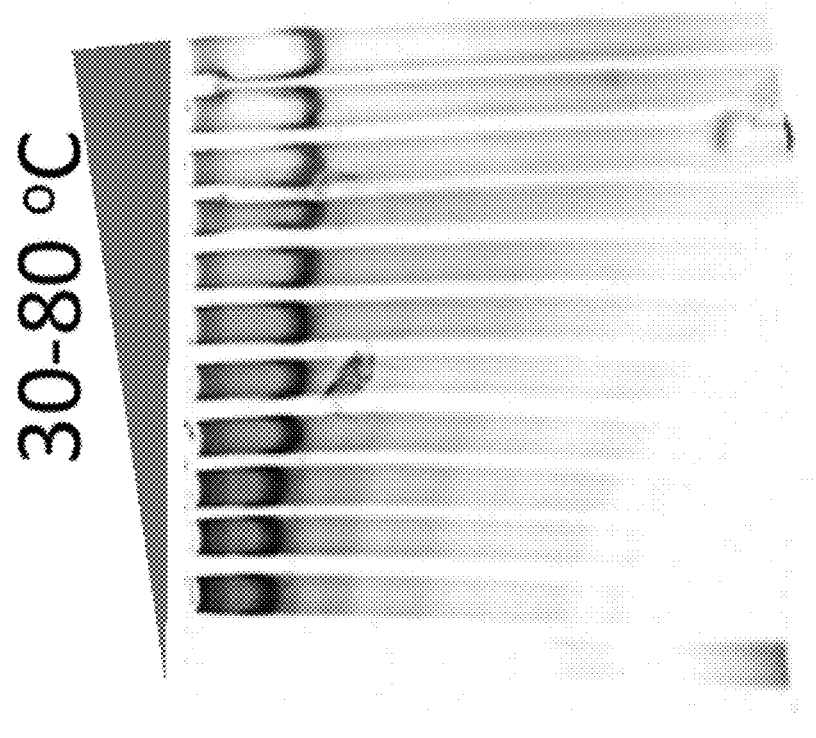
FIGS. 6A to 6D show thermal stability (Tm) of designed RNA nanoparticles.
Figure 6A:
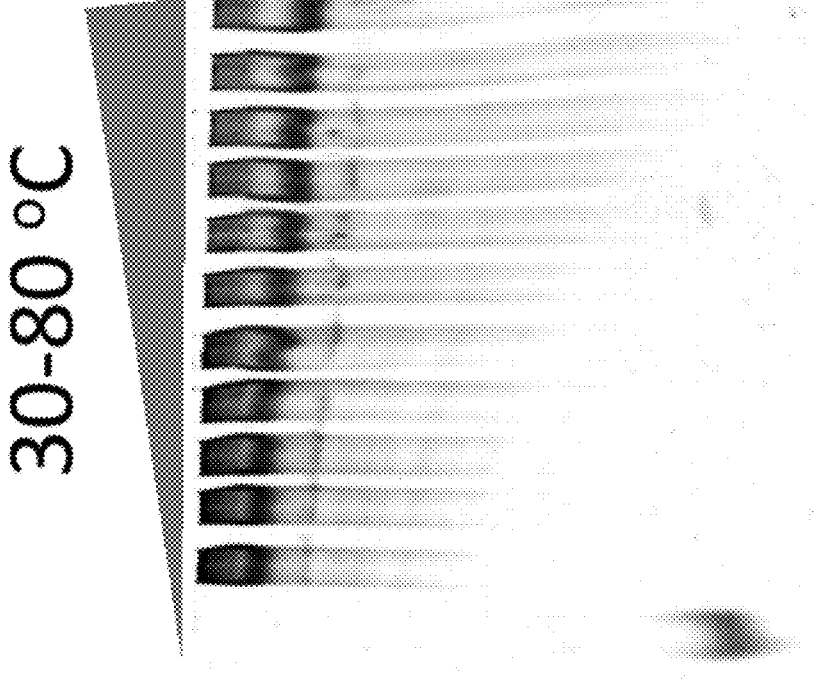
Figures 6C, 6D:
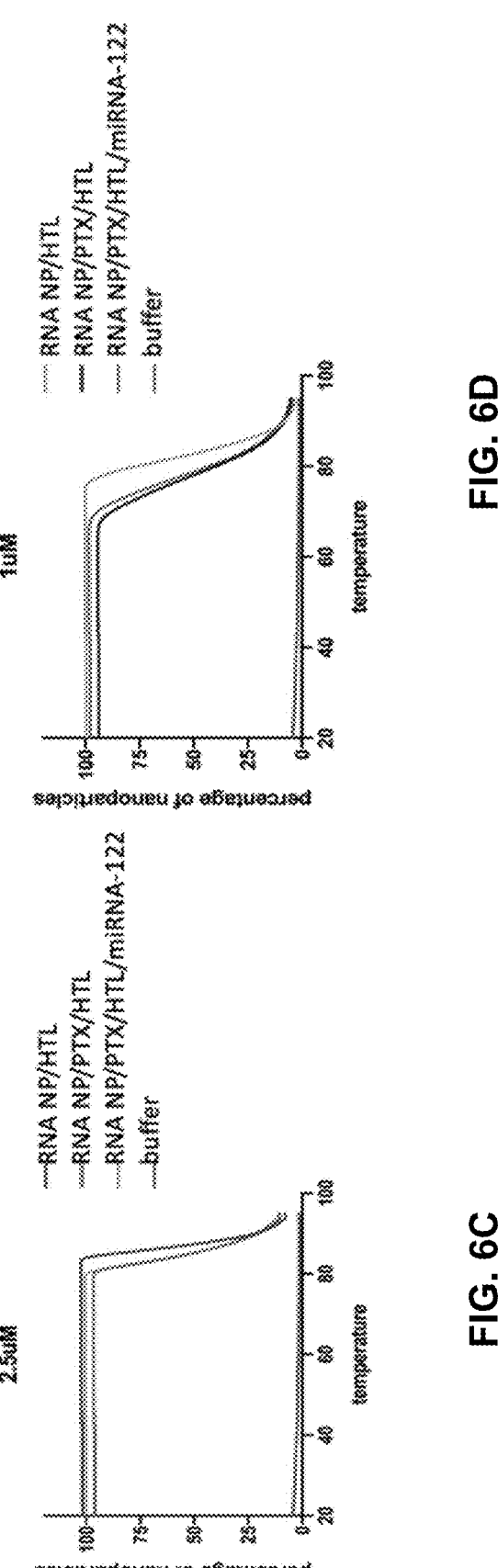

The thermal stability of the RNA nanoparticles should be higher than physiological temperature (37° C.) for the efficient delivery of drugs. Therefore, thermal stability of the composed RNA nanoparticles was assessed using Temperature Gradient Gel Electrophoresis (TGGE) and real time PCR. The thermal melting (Tm) of the RNA nanoparticles harboring the two drugs and the hepatocyte targeting ligand exhibited a Tm of ~67.5° C., whereas the RNA nanoparticles without miR-122 sequence showed a Tm of –80° C. (FIG. 6C). The results were further confirmed by real-time PCR (FIG. 6D). All the RNA strands were mixed at equimolar concentrations in the presence of 1×SYBR Green II dye at 2.5 µM and 1.0 µM concentrations to create RNA nanoparticle PTX & miR-122 along with trivalent galactosamine derivative and results were compared to the Tm of control nanoparticles (without drugs and targeting ligands). The nanoparticle samples were heated to 95° C. for 5 min then slowly cooled to 20° C. at a rate of 0.11° C./s using a Roche Lightcycler 480 real-time PCR machine. The RNA nanoparticle formation was monitored by measuring fluorescence levels at 480.0 nm excitation. The thermal melting values for RNA/PTX/miR-122/HTL nanoparticle found to be 80° C. and approximately 67.5° C. at 2.5 uM and 1.0 µM respectively and these Tm values are close to that of control RNA nanoparticles (see FIG. 6D). The Tm values of the RNA nanoparticles were far higher than physiological temperature (37° C.), indicating that the RNA nanoparticles can remain intact at physiological temperature and at lower concentrations.

Figure 7:
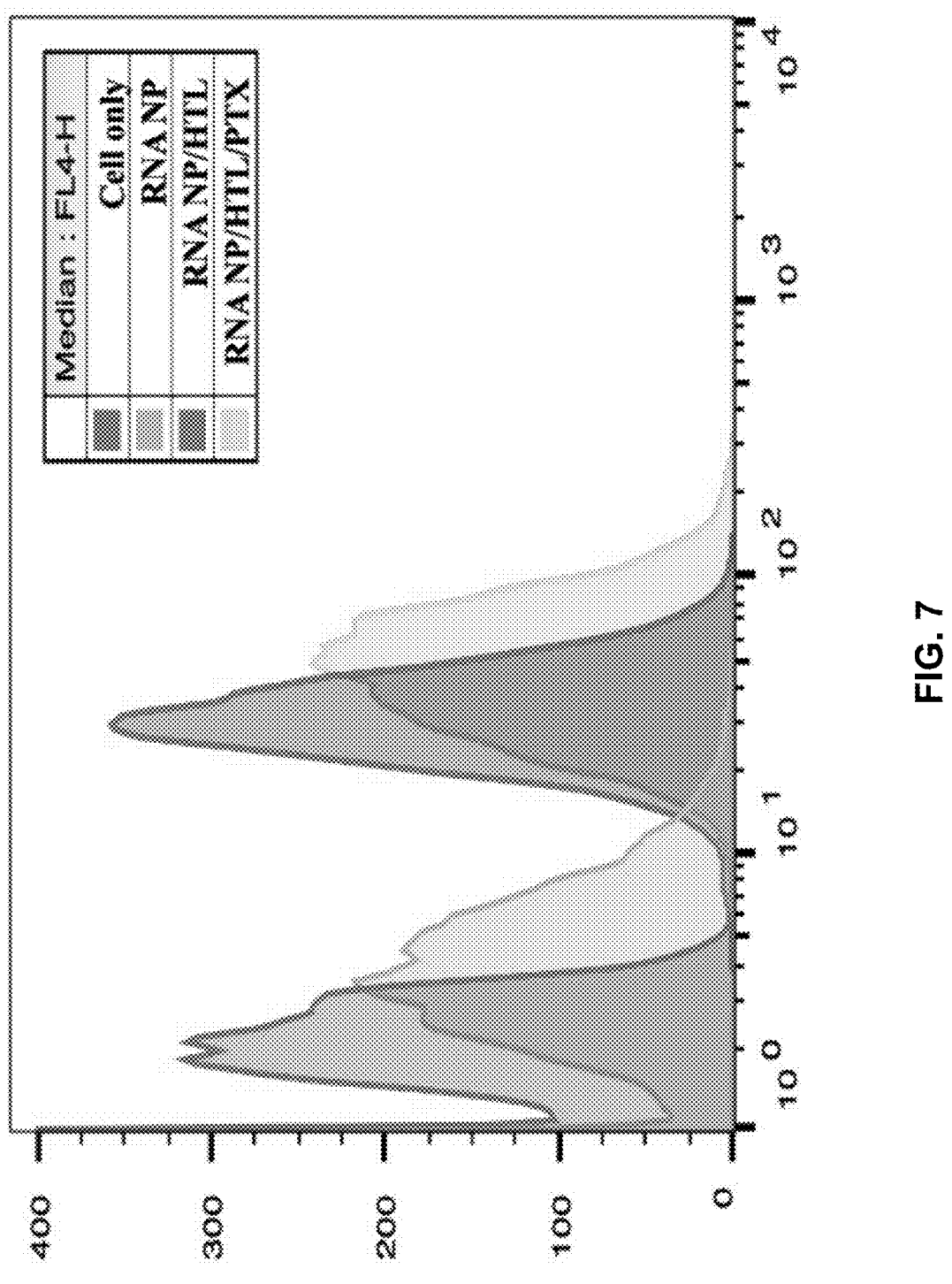
FIG. 7 shows flow cytometry showing the binding of RNA nanoparticle-binding capability to ASGP-R positive HepG2.

The in vitro cell binding affinity between RNA nanoparticles harboring HTLs and ASGP-R expressing HepG2 cells were evaluated and the results compared with control RNA nanoparticles. Fluorophore (Alexa-647) labeled RNA/PTX/HTL/miR-122 nanoparticle (100 nM) and the control (without drugs/targeting ligands) RNA nanoparticle were incubated with ASGP-R positive Hep G2 cells at 37° C. for 1 h. After 1 h incubation, the cells were trypsinized, washed and resuspended in PBS and subjected for flow cytometry analysis. The results showed that the RNA nanoparticle harboring HTLs have strong binding affinity to ASGP-R positive cells (FIG. 7). On the contrary, RNA nanoparticle without HTLs did not bind to ASGP-R positive cell line (FIG. 7). The results indicating that the RNA nanoparticles with hepatocyte targeting ligands (HTLs) can deliver the drugs to the hepatocyte cells selectively with high affinity.

Figure 8A:
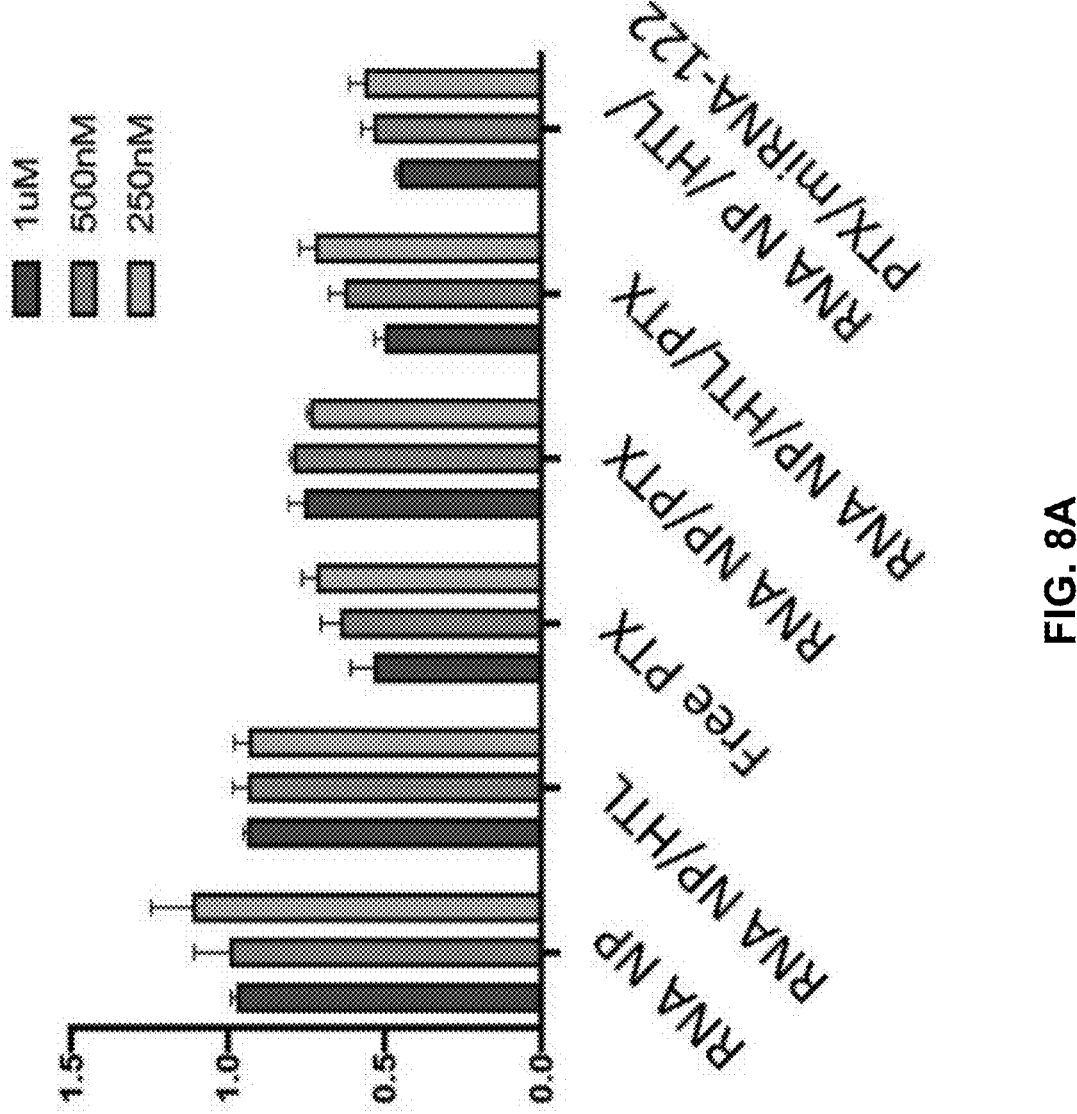
FIG. 8A shows MTT assay demonstrating cytotoxicity of RNA nanoparticles to HepG2 cells.

In order to assess the cytotoxicity of the designed RNA nanoparticles, HepG2 cells were incubated with the RNA nanoparticles at various concentrations (1 µM, 500 nM, and 250 nM) along with the control RNA nanoparticles. MTT assay was performed to test the cytotoxicity. In brief, $1×10^4$ HepG2 cells were seeded into 96-well plates for 24 h prior to the treatment. Then, the cells were incubated with 1 µM, 500 nM, and 250 nM of the designed RNA nanoparticles and the controls in triplicate. The plate was further incubated for 48 h, then 15 µl of MTT dye solution was added to each well and incubated it for 4 more hours at 37° C. Next, a 100 µL of stop mix was added to each well and incubated for 4 hours to get a uniformly colored solution. The cytotoxicity of the RNA nanoparticles was measured by means of absorbance recorded at 570 nm using microplate reader. All the RNA nanoparticle conjugated with paclitaxel shows cytotoxicity. RNA nanoparticle bearing both PTX, miR-122 along with hepatocyte targeting ligands exhibited higher toxicity compared to control RNA nanoparticles, moreover, the results are close to that of Paclitaxel itself (FIG. 8).

Figure 8B:
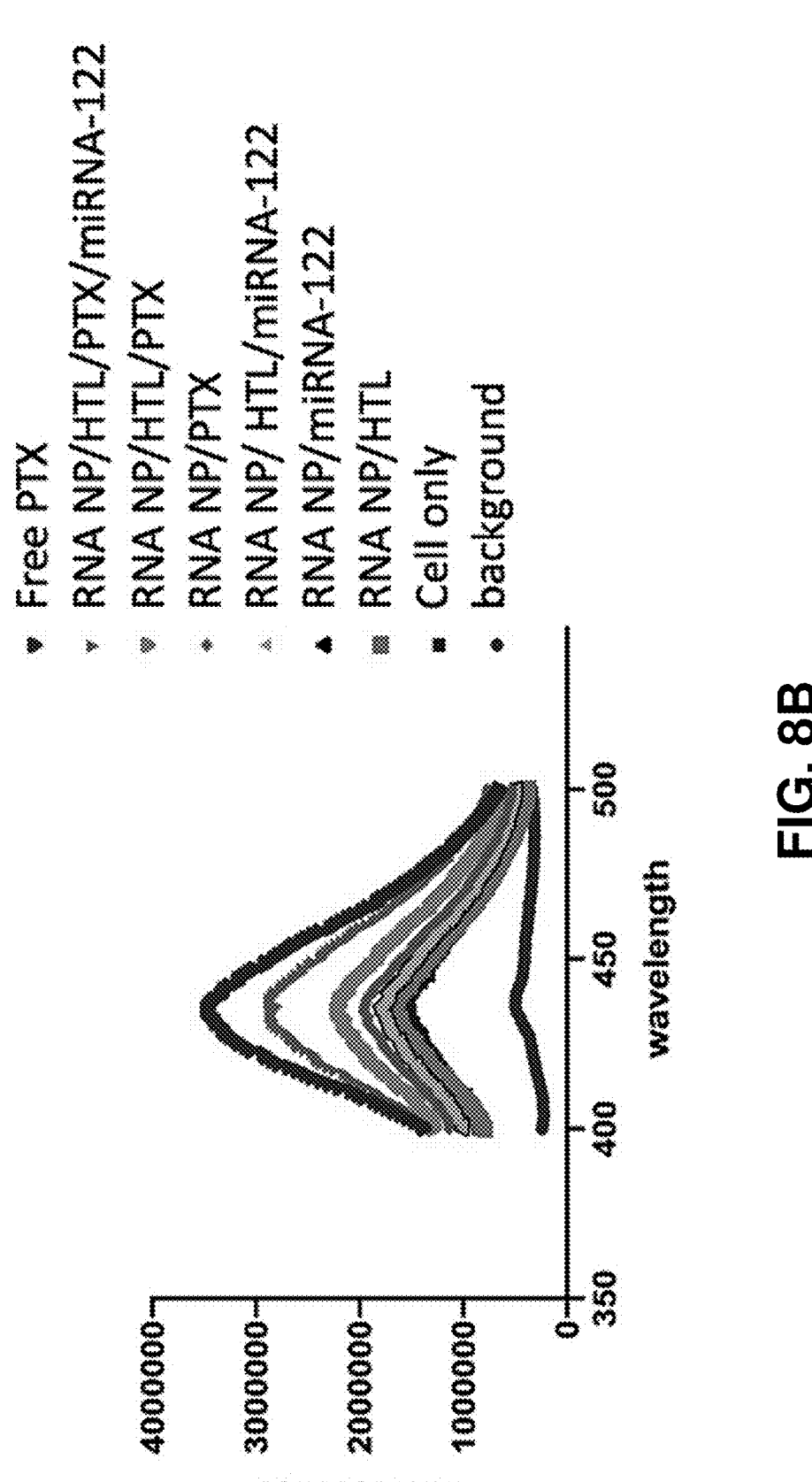
FIG. 8B shows caspase-3 assay exhibiting cell apoptosis induction after treatment.
Figure 9A:
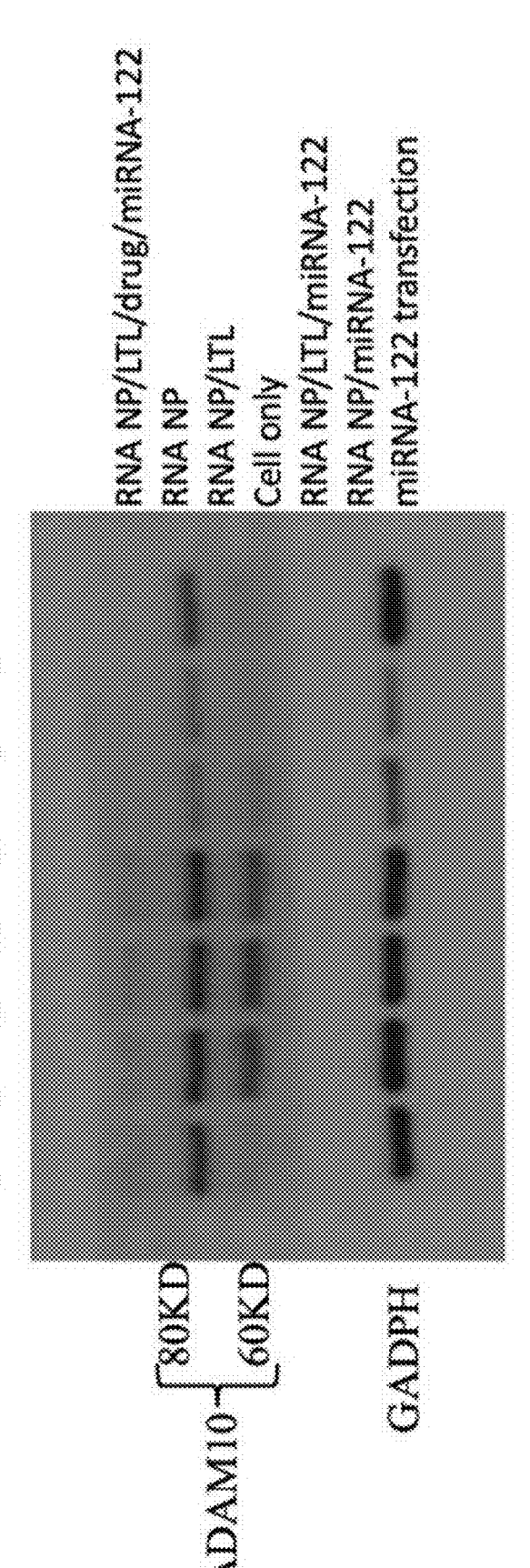
FIG. 9A is a western blot showing the effect of miR-122 knock-down on the downstream protein ADAM10 expression.
Figure 9B:
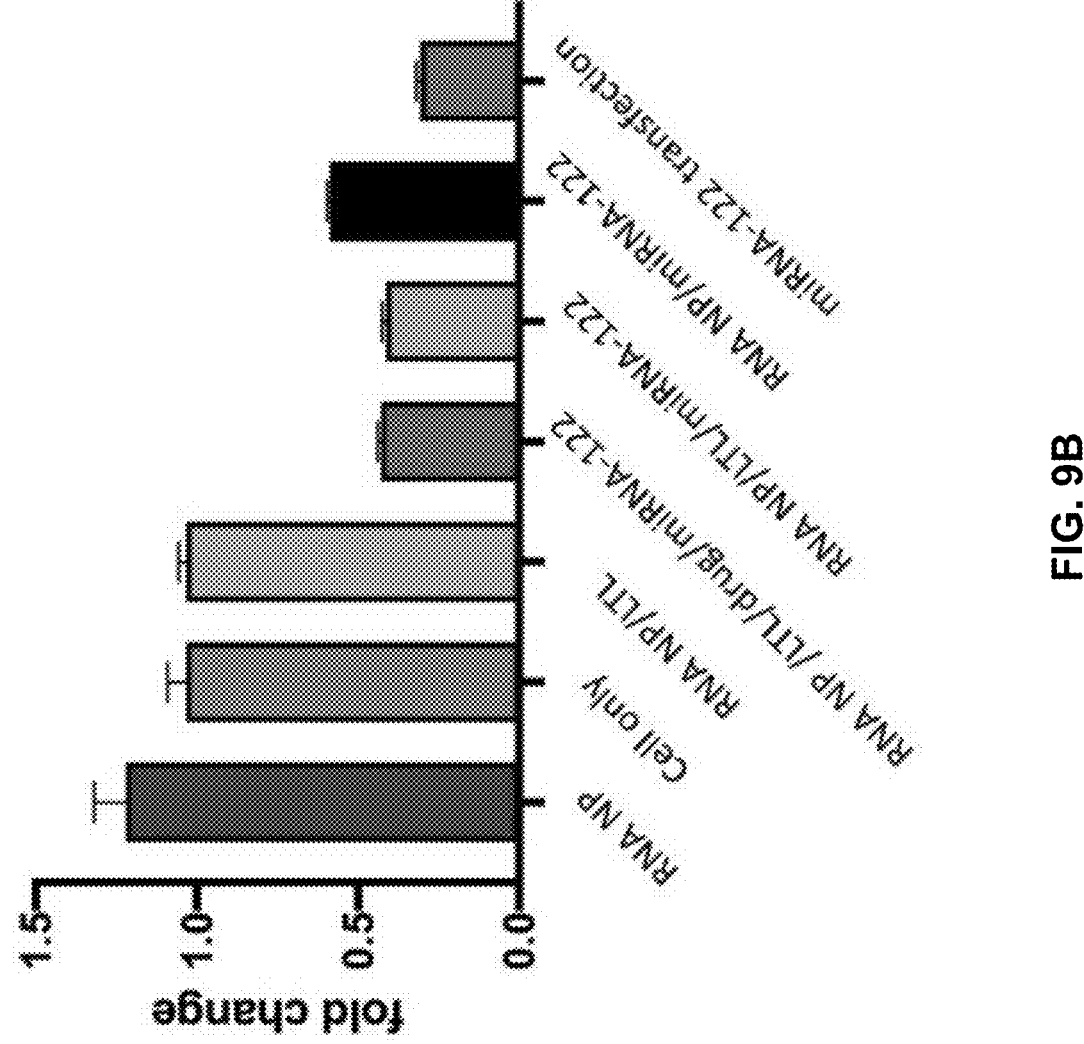
FIG. 9B shows quantification of protein ADAM10 expression using ImageJ software.

Example 2: Effect of RNA Nanoparticles Harboring Paclitaxel, miR-122, and Three Parallel 4-(((2R,3R, 4R,5R,6R)-3-acetamido-4,5-dihydroxy-6-(hy-droxymethyl) tetrahydro-2H-pyran-2-yl)oxy)-N-(6-(4,4-bis(hydroxymethyl)piperidin-1-yl)-6-oxohexyl) butanamide on Early Apoptosis The effect of miR-122 and paclitaxel on early apoptosis was studied by measuring caspase-3 marker levels in HepG2 cells. HepG2 cells were treated with 400 nM of the RNA/PTX/miR-122/HTL nanoparticles and its controls and incubated at 37° C. for 24 hrs. Then, the cells were lysed using the cold cell lysis buffer, and for each 25 µL of cell lysate, 2 µL of reconstituted Ac-DEVD-AMC in 80 µL of HEPES buffer was added and incubated at 37° C. for 1 h. The amount of caspase-3-AMC substrate released from Ac-DEVD-AMC was measured by means of fluorescence intensity at 400-500 nm window with an excitation of 380 nm (FIG. 8B). The cells treated with RNA nanoparticles shows higher early apoptosis. Combination of paclitaxel and miR-122 has the highest early apoptosis effect, which demonstrate the synergetic effect between paclitaxel and miR-122. The effect of miRNA was further examined by measuring downstream protein expression in HepG2 cells using western blot assay. The HepG2 cells were seeded on a 24-well plate in 10% FBS medium overnight at 37° C. Cells were then treated with 400 nM of RNA/PTX/miR-122/HTL and the control groups (RNA/miR-122, RNA/miR-122/HTL, RNA/HTL) then incubated for 72 h. The cells were lysed in RIPA buffer with protease inhibitor and the downstream protein ADAM10 concentration was quantified by BCA Protein Assay Kit. A total of 10 µg of protein was loaded to 10% SDS PAGE and run for 1 h. The gel was transferred to polyvinylidene fluoride membrane and followed by blocking in 5% fat-free milk at room temperature for 2 h. The membrane was then stained with primary antibody (rabbit-ADAM 10: 1:1000; mouse-GADPH: 1:10 000) at 4° C. overnight and washed thrice for 15 min using TBST. The membrane was then stained with secondary antibody (goat pAb to rabbit IgG and goat pAb to mouse IgG: 1:20 000) at room temperature for 1 hour and washed thrice for 15 min using TBST. Membranes were then incubated with ECL substrate, exposed to Amersham Hyperfilm™ together, and processed with a Series 2000A Processor film developer (TiBA, FIG. 9). Compared with control groups, Nanoparticles harboring miR-122 could knockdown the ADAM 10 protein expression. The result demonstrates the delivery of miR-122 using RNA nanoparticles is successful. Furthermore, nanoparticles harboring HTLs show higher knockdown efficiency, which demonstrate the potential of target specific delivery using hepatocyte targeting ligand.

Figures 10A, 10B:
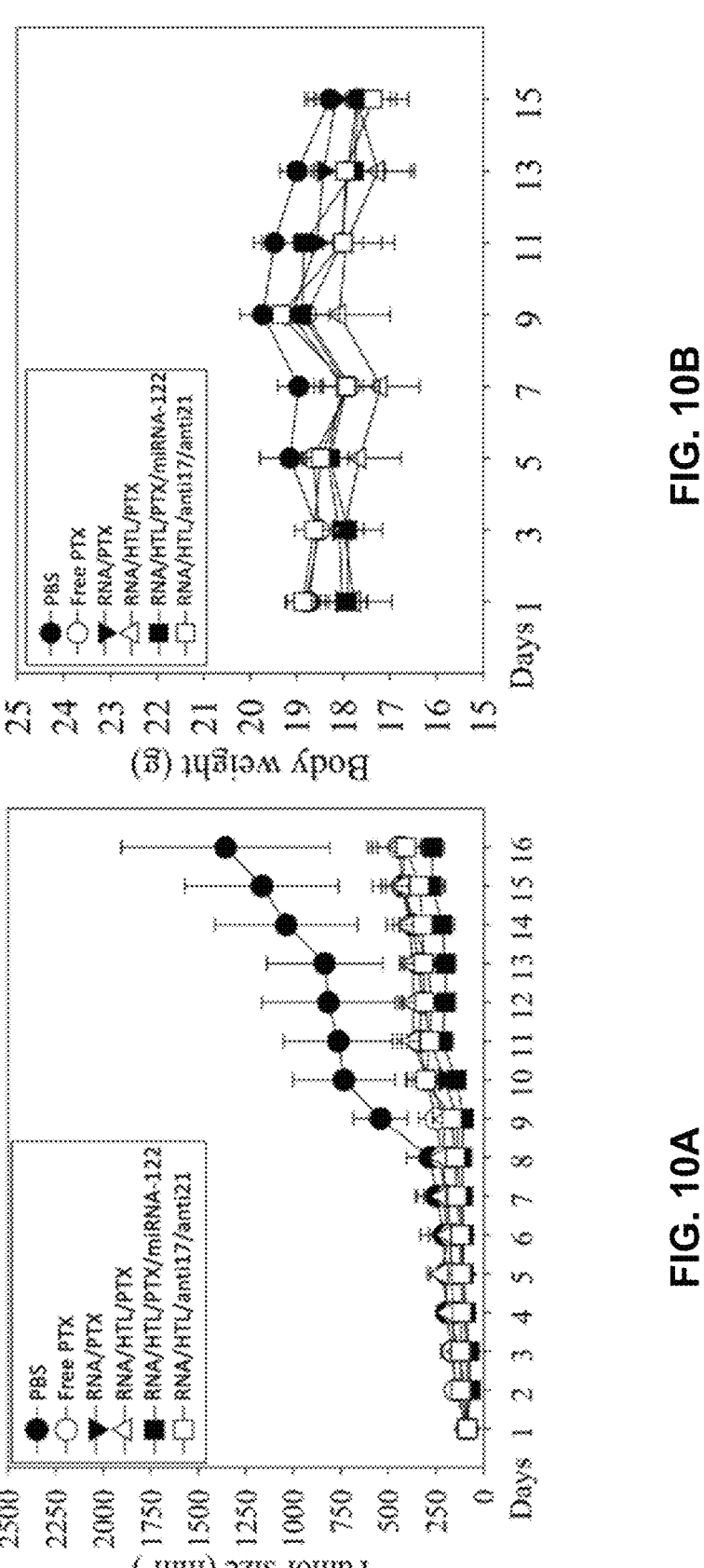
FIG. 10A shows in vivo tumor growth curve over the course of 5 injections assay the tumor inhibition effect of RNA nanoparticles harboring PTX, miR-122 and controls.
FIG. 10B shows mice body weight curve demonstrate no side effect.
Figure 11:
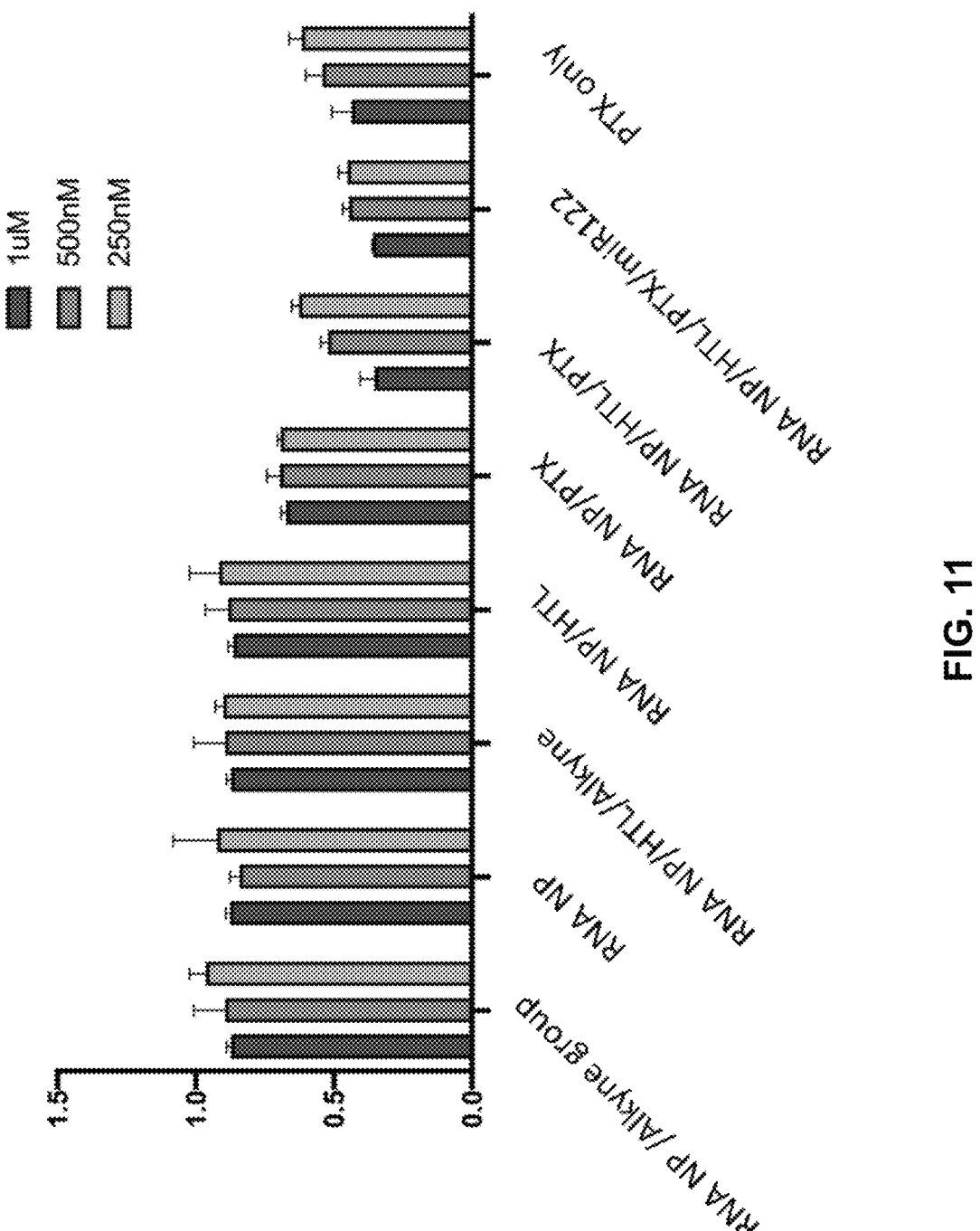
FIG. 11 shows MTT assay demonstrating cytotoxicity of RNA nanoparticles to liver cancer cells. MTT result demonstrated all the RNA nanoparticle conjugated with PTX shows cytotoxicity. RNA nanoparticle bearing both PTX, miRNA-122 along with HTL exhibited higher toxicity compared to control RNA nanoparticles. Compared with PTX only, the RNA nanoparticles also showing better and concentration dependent toxicity.

Example 3: Effect of RNA Nanoparticles Harboring PTX, miR-122, and Three Parallel 4-(((2R,3R,4R, 5R,6R)-3-acetamido-4,5-dihydroxy-6-(hydroxymethyl)tetrahydro-2H-pyran-2-yl)oxy)-N-(6-(4,4-bis (hydroxymethyl)piperidin-1-yl)-6-oxohexyl) butanamide on Tumor Growth Reduction The therapeutic effect of RNA/PTX/miR-122/HTL nanoparticles was validated by a tumor inhibition study in a hepatocellular carcinoma HepG2 xenograft model in nude mice. HepG2 tumor xenografts were established by subcutaneously injecting $2 \times 10^6$ HepG2 cells/100 mL PBS into the nude mice. When the tumor volume reached about 80 mm³, the mice were randomly divided into two groups (n=6). The mice of the therapeutic group were injected with RNA/PTX/ miR-122/HTL nanoparticles and control nanoparticles. A total of 5 injections (5 mg/kg, PTX/body weight) was performed every other day. The tumor volume ((length*width2)/2) was measured and recorded accordingly. Treatment with nanoparticles significantly inhibited tumor growth in the xenograft model compared with the control group (FIG. 10A). Furthermore, the mice body weight didn't have significant change demonstrate the treatment with RNA nanoparticles have limited side effect (FIG. 10B).

Figure 12B:
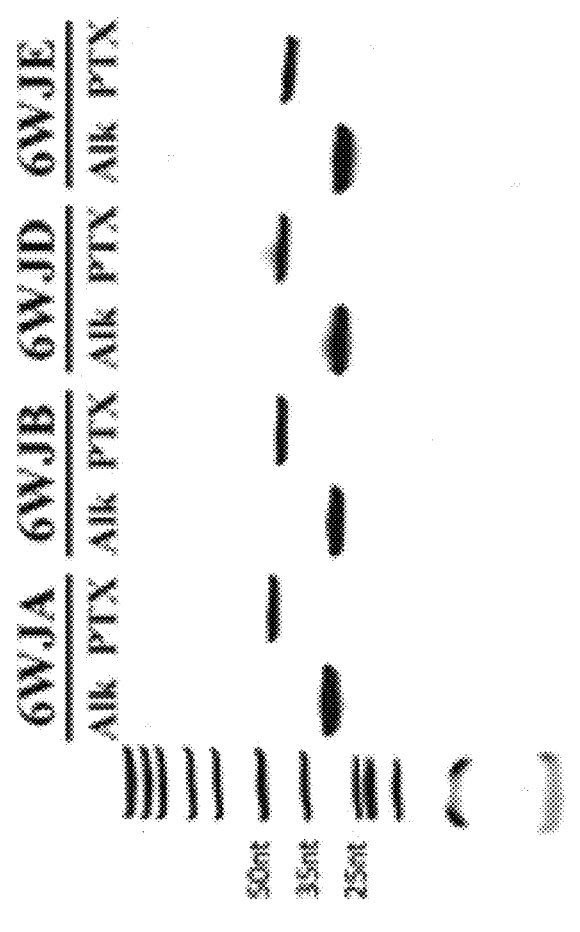
FIGS. 12A to 12D show design and construction of 6WJ/HTL/PTX/miR122 RNA nanoparticles.
Figure 12A:
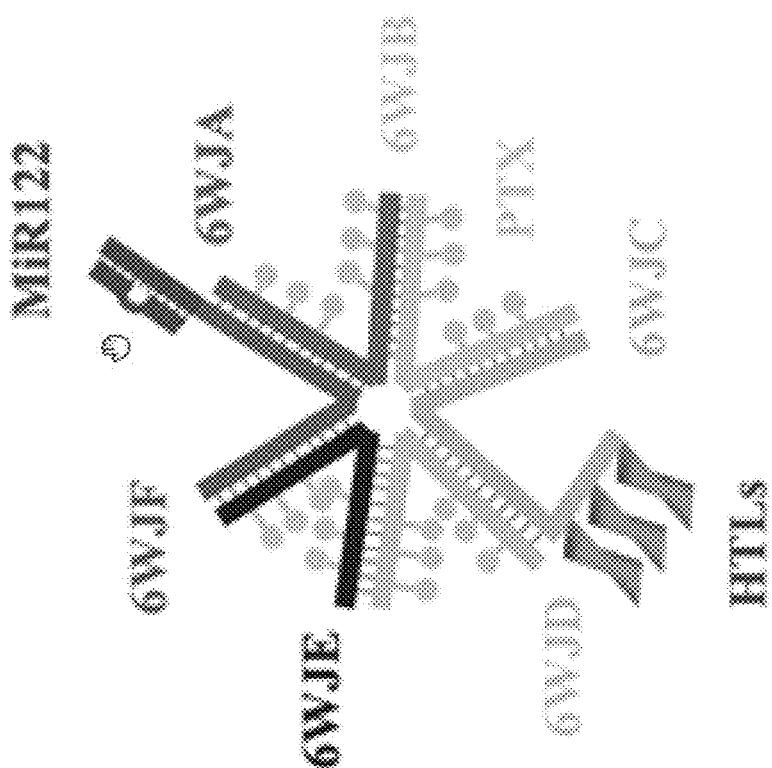
Figures 12C, 12D:
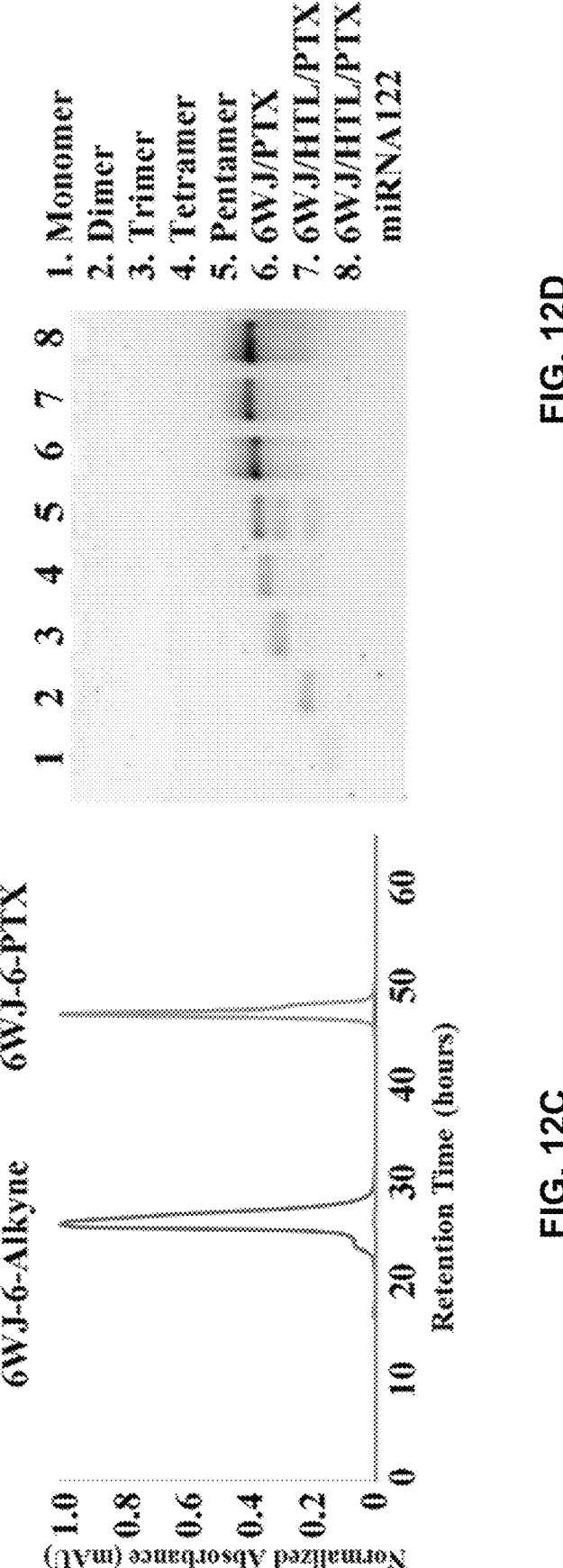

Example 4: Multivalent Rubber-Like RNA Nanoparticles for Targeted Co-Delivery of Paclitaxel and MiRNA to Silence the Drug Efflux Transporter and Liver Cancer Drug Resistance Results and Discussion
Design, Construction, and Characterization of RNA Nanoparticles Harboring miR-122, PTX, and Hepatocyte Targeting Ligands
The 6WJ RNA nanoparticle was constructed by a modular design and was composed of six component RNA strands. These RNA strands self-assembled into a globular structure with six RNA strands when mixed at an equimolar concentration using an annealing process (FIG. 12A). To improve the thermal stability and confer the RNase resistance, 2'-Fluoro modified pyrimidines were incorporated into the growing RNA strands during the solid phase synthesis. Each 6WJ-A, -B, -D, and -E strand were synthesized with 6-copies of alkyne functionalities for conjugating the prodrug PTX-azide. The PTX-azide was synthesized using an esterification reaction between the hydroxyl of the paclitaxel and the carboxyl of 6-azidohexanoic acid. The PTX-azide was successfully conjugated to the RNA-alkyne strands using Cu(I)-catalyzed azide-alkyne cycloaddition (CuAAC) click reaction, evident from gel electrophoresis and HPLC (FIGS. 12B & 12C). The 6WJ-C RNA strand was conjugated with hepatocyte targeting ligands (HTLs) and 6WJ-F RNA strand was extended with miR122 sequence (FIG. 12A). The multivalent RNA nanoparticle 6WJ/HTL/PTX/miR122 was constructed by mixing the RNA strands harboring miR122, PTX, and HTLs at a stoichiometric ratio using a bottom up self-assembly method. The RNA nanoparticles were assembled with high efficiency as shown in gel shift assay with a stepwise assembly of the complex (FIG. 12D).

Figure 13A:
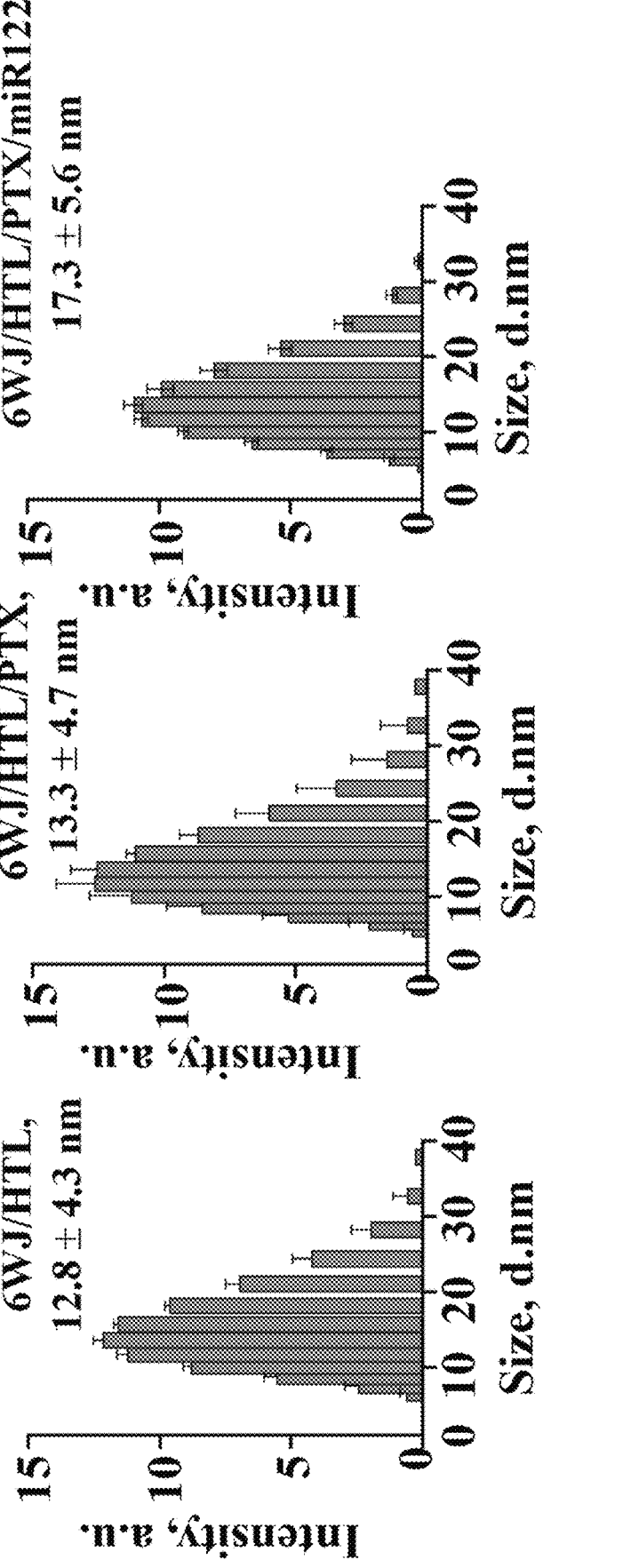
FIGS. 13A to 13C show characterization of 6WJ/HTL/PTX/miR122 RNA nanoparticles.
Figure 13B:
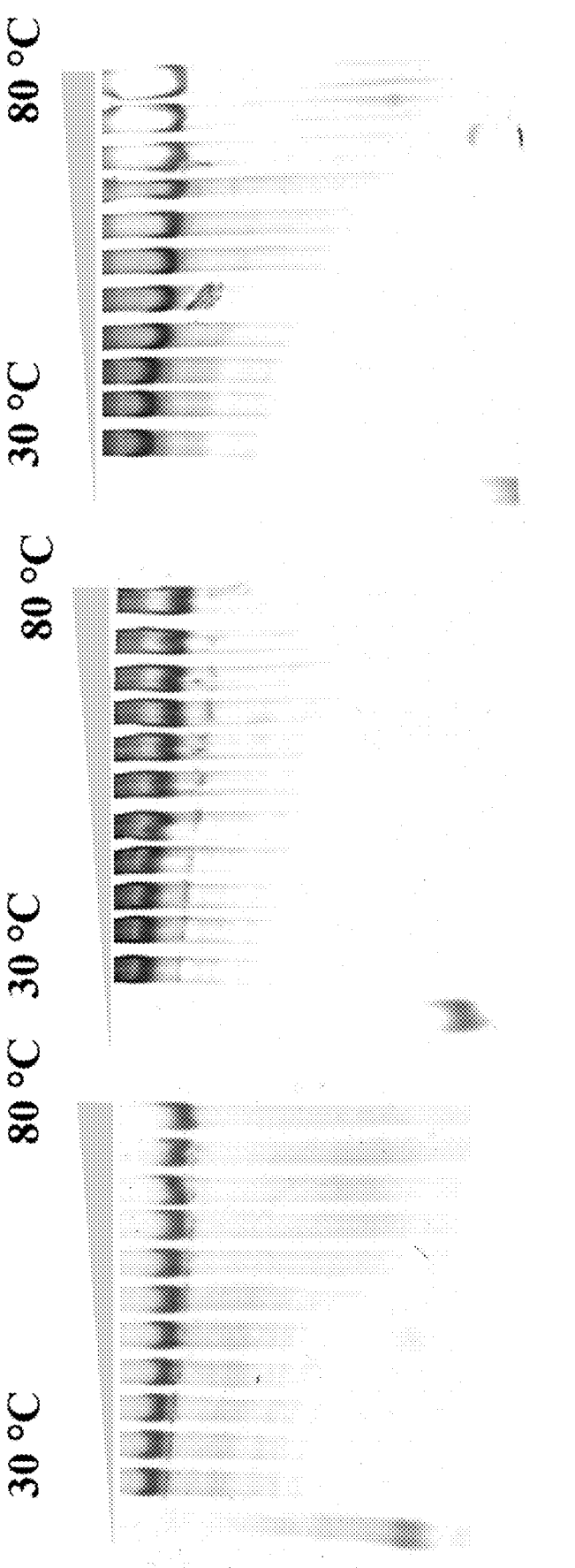
Figure 13C:
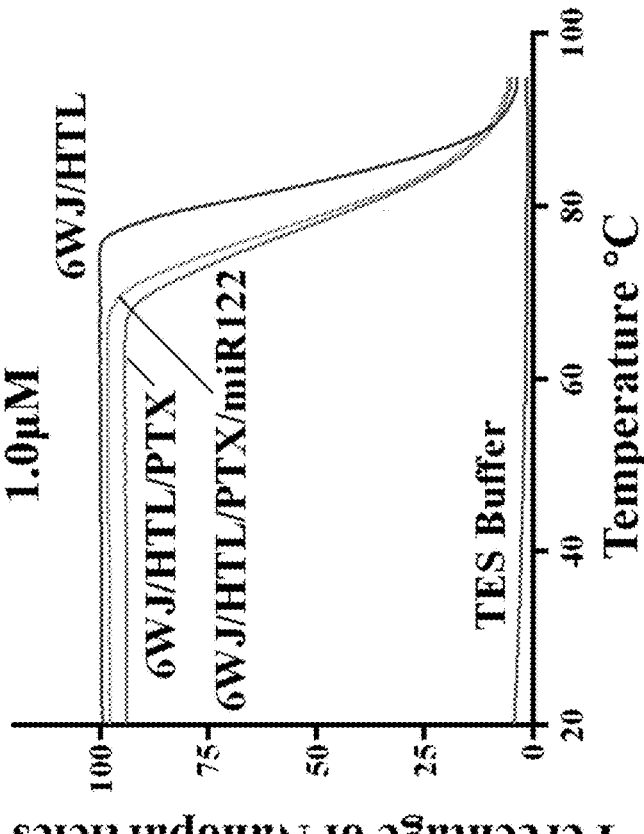
Figure 13C:
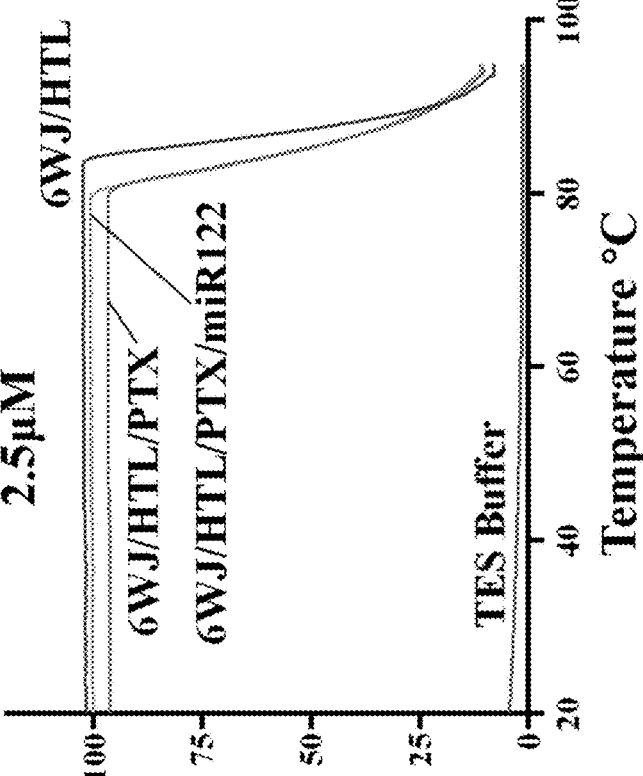
Figure 14A:
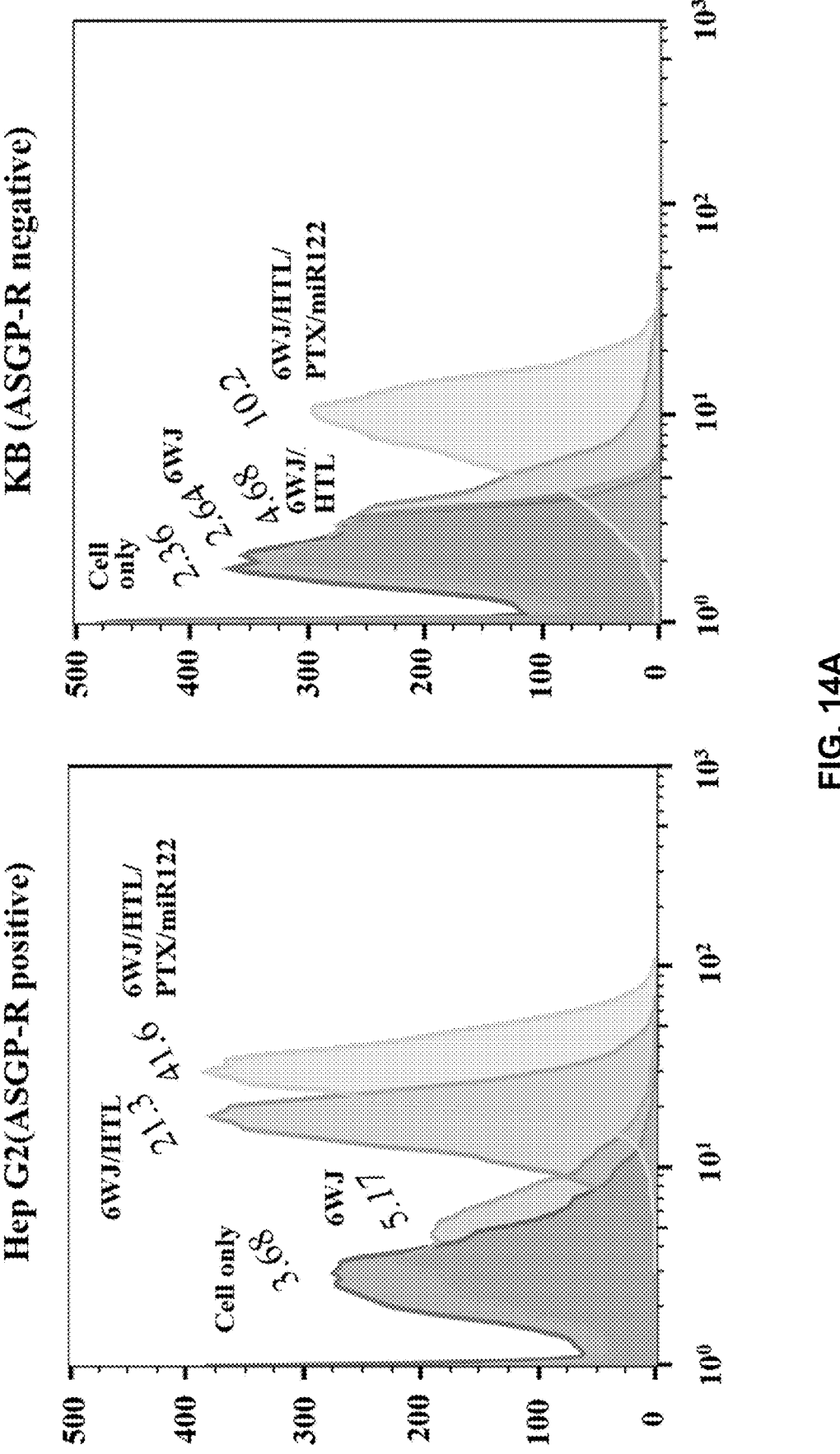
FIGS. 14A to 14D show in vitro binding affinity, specificity, and internalization studies of the 6WJ RNA nanoparticles harboring hepatocyte targeting ligands.
Figure 14C:
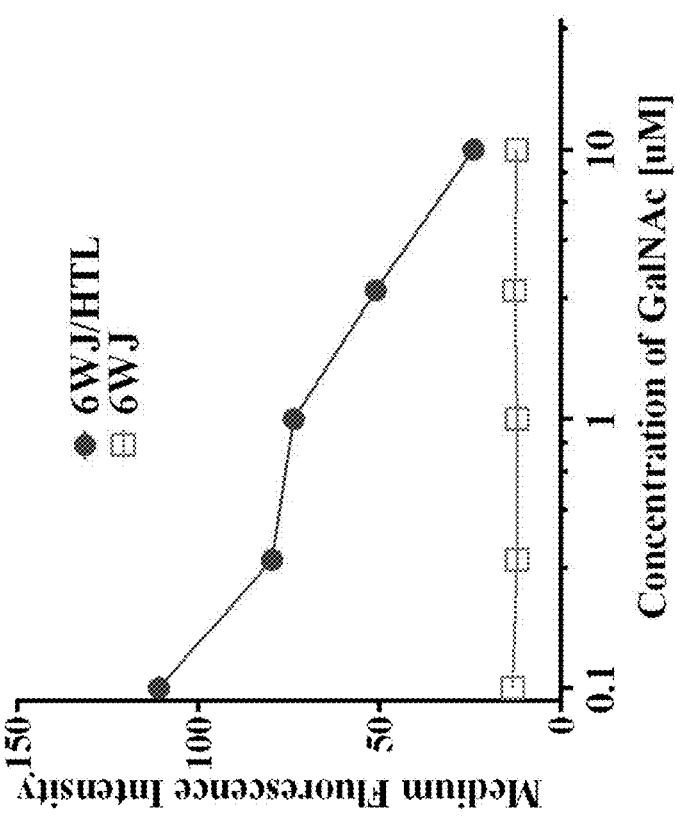
Figure 14B:
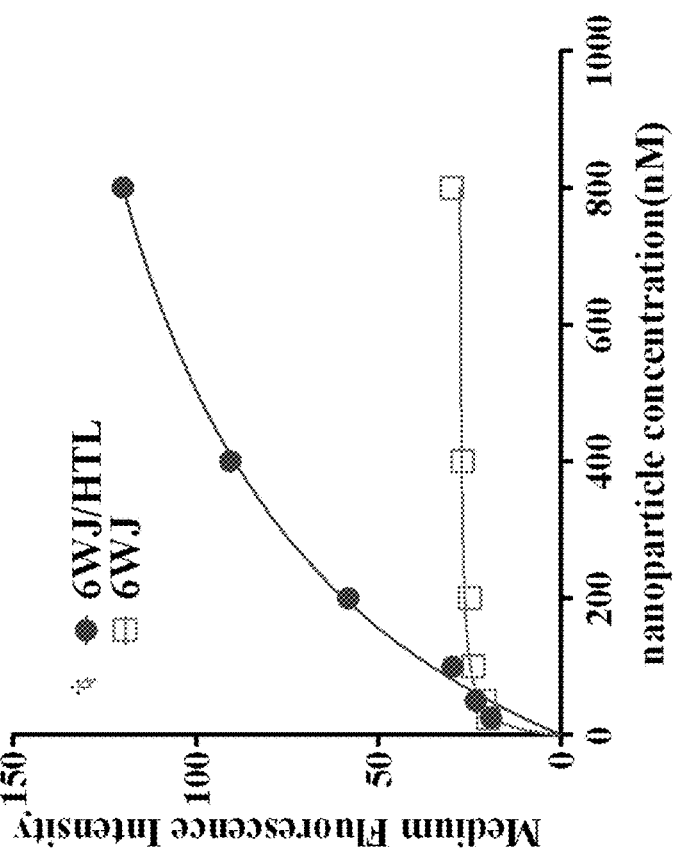
Figure 14D:
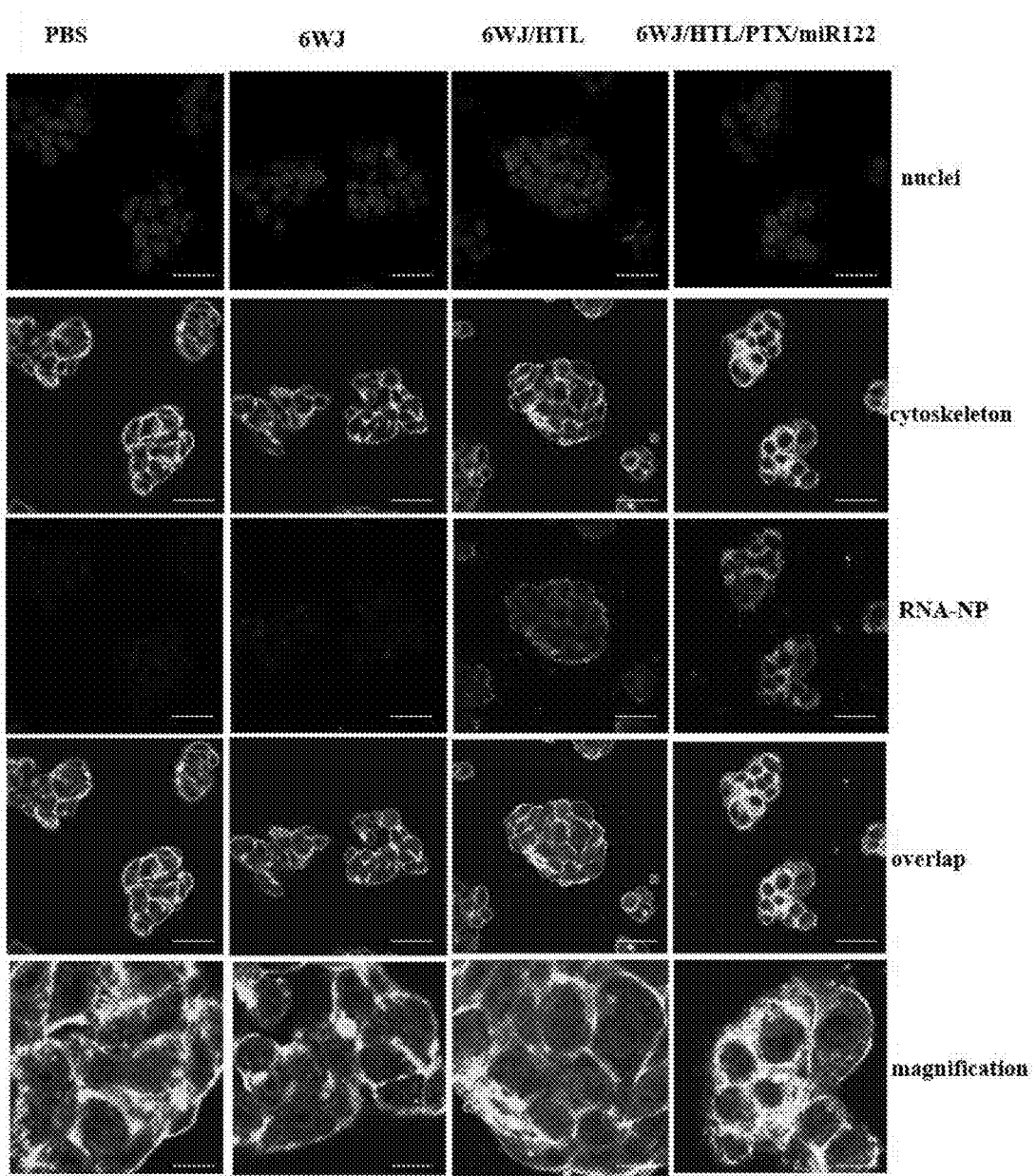

The 6WJ/HTL/PTX/miR122 nanoparticles along with control nanoparticles 6WJ/HTL and 6WJ/HTL/PTX were measured for their average hydrodynamic diameter using Dynamic Light Scattering (DLS) and were shown to be 12.83±4.3 nm, 13.33±4.7 nm, and 17.27±5.6 nm in size, respectively (FIG. 13A). The values indicated that the average size of the RNA nanoparticle increased from 6WJ/HTL to 6WJ/HTL/PTX/miR122, which is as expected due to additional functional groups. The thermal stability of the nanoparticles was determined by melting temperature ($T_m$) by Temperature Gradient Gel Electrophoresis (TGGE) assay. The Tm values were found to be above 80° C. for the 6WJ/HTL, 6WJ/HTL/PTX nanoparticles and approximately 70° C. for 6WJ/HTL/PTX/miR122 nanoparticle (FIG. 13B). The thermal stability was further evaluated by annealing temperature ($T_a$) by thermal cycler at different concentrations. The $T_a$ values were above 80° C. at 2.5 µM for all three nanoparticles while slight reduction in Ta was observed for 6WJ/HTL/PTX/miR122 at 1.0 µM (Ta=approximately 70° C., FIG. 13C). Both the $T_m$ and $T_a$ values indicated that the RNA nanoparticles were stable enough to remain intact even at ultra-low concentrations. The results demonstrated that the multifunctional RNA nanoparticle with a defined size (17.7 nm), and high thermodynamic stability could serve as a stable scaffold for targeted delivery of the combination therapeutics for the HCC treatment.
Binding Affinity, Specificity, and Internalization of RNA Nanoparticles to ASGP-R Expressing HepG2 Cells
Targeted delivery of anticancer drugs using nanoparticles not only depends on their ability to induce an EPR effect but also specifically target and internalize into targeted cancer cells. N-acetyl-galactosamine has been widely reported as an ASGP receptor targeting ligand overexpressed on the hepatocyte surface and facilitates cellular internalization. Therefore, three galactosamine ligands were conjugated to the RNA nanoparticles in a series and studied their binding affinity, specificity, and cellular uptake abilities by labeling a near infrared fluorophore (Alexa 647) as a marker onto the 6WJ. The flow cytometry results indicated that the RNA nanoparticles harboring targeting ligands exhibit higher binding affinity compared to nanoparticles with no ligands present (FIG. 14A). The dissociation constant ($K_d$) for the 6WJ/HTL nanoparticles was found to be around 0.4 µM for ASGP-R expressing HepG2 cells (FIG. 14B). Additionally, the RNA nanoparticles showed very little binding to ASGPR negative KB cells, indicating their specificity for hepatocytes (FIG. 14A). To further demonstrate that the binding affinity is attributed to the ASGP-R and ligand interaction, a binding inhibition assay was performed using a competitive inhibitor, free N-Acetylgalactosamine. The 6WJ/HTL nanoparticles binding for HepG2 cells was drastically inhibited as the free galactosamine concentration increased. In contrast, control experiments did not show any difference as concentration of free galactosamine increases (FIG. 14C), demonstrating the RNA nanoparticles specificity for ASGPR expressing HepG2 cells. These results demonstrated that RNA nanoparticles bind to ASGP-R expressing HepG2 cells with high specificity.
Cellular internalization is the key to achieve the therapeutic effect of the RNA nanoparticles. Therefore, the nanoparticles' cellular internalization ability was further assessed using confocal microscopy. The cellular internalization of the RNA nanoparticles is clearly evident by their strong co-localization with cytoplasm that resulted in a yellow color (overlaid image of red color form RNA nanoparticle & green color from cytoplasm, FIG. 14D). Whereas, cells incubated with control RNA nanoparticles (without targeting ligand) shown less nonspecific uptake. Overall, the results demonstrated that the RNA nanoparticles harboring hepatocyte targeting ligands bound strongly to ASGP-R expressing HepG2 cells with high specificity that favored their strong cell uptake efficiency through ASGP-Rs.

Downregulation of the Oncogenic Protein Expression by RNA Nanoparticles Harboring miRNA122

Figure 15A:
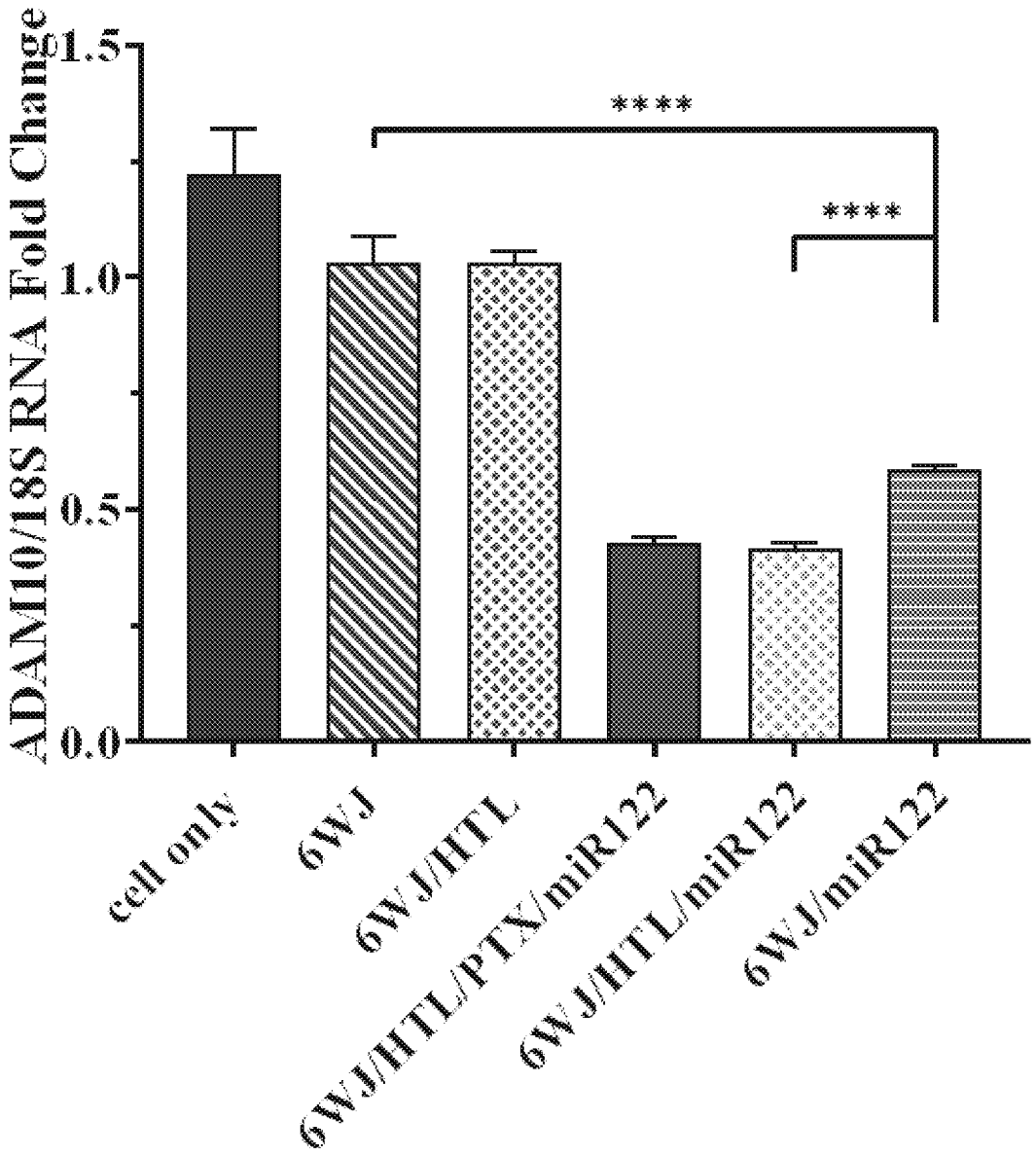
FIGS. 15A to 15C show in vitro assay for the silencing of the oncogenic protein ADAM10 and the drug transporter MDR1 (P-gp) by 6WJ/HTL/miR122 nanoparticles.
Figure 15B:
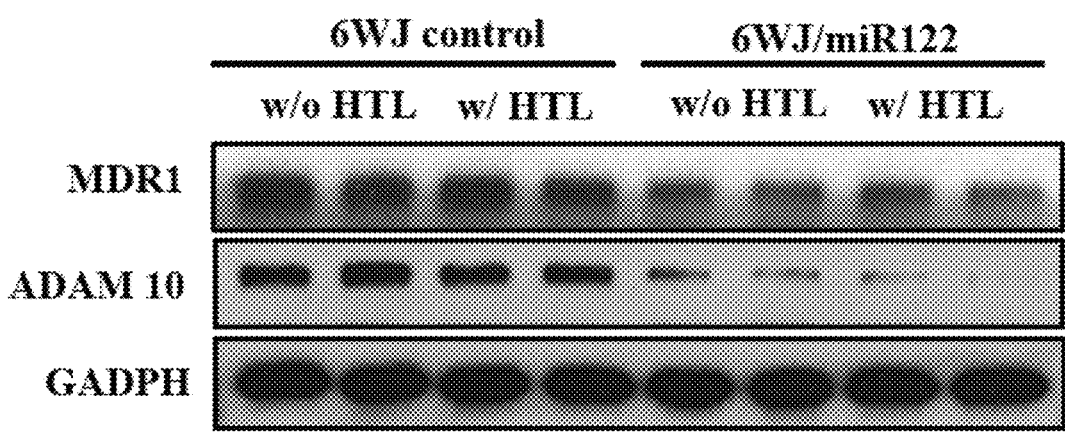
Figure 15C:
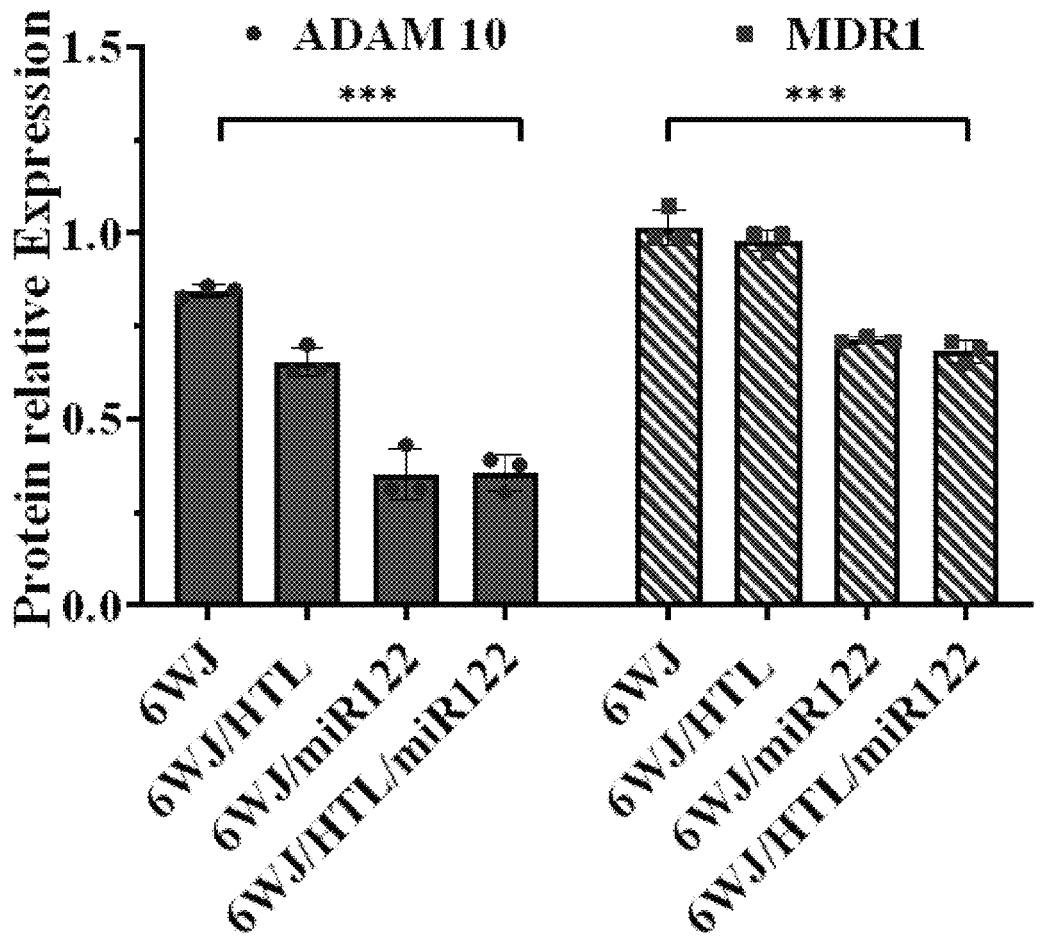

The liver-specific miR122 regulates a set of genes and maintains liver integrity, however, miR122 is frequently suppressed in HCC leading to its proliferation and drug resistance. Therefore, the miR122 was delivered to HepG2 cells to suppress the tumorigenic proteins using the RNA nanoparticles. Downregulation of the oncogenic a disintegrin and metalloproteinase domain-containing protein 10 (ADAM10) expression was taken as a parameter to study the function of miR122 in HepG2 cells. The HepG2 cells were incubated with RNA nanoparticles harboring miR122 and control nanoparticles, then the cells were processed and measured for the expression of ADAM10 mRNA and protein expression using the real-time PCR and Western blot, respectively. The treatment groups with nanoparticles harboring miR122 showed significant suppression of the ADAM10 gene (FIG. 15A) as well as protein expression (approximately 2-3 fold) whereas the cells treated with control nanoparticles did not show inhibited protein expression (FIGS. 15B & 15C). The downregulation of the ADAM10 gene and protein expressions is a clear indication of the RNA nanoparticles ability to deliver the miR122 to hepatocyte cells and exercise its function in gene regulation.

Downregulation of Drug Efflux Transporters Expression by RNA Nanoparticles Harboring miRNA122

The miR122 is also known to sensitize HCC tumor cells to chemical drugs by modulating multi-drug resistance (MDR) related genes that are associated with drug transporters such as multi-drug resistance protein 1 (MDR1). MDR1 is a drug efflux transporter also referred as P-glycoprotein (P-gp) that expels drugs from the cell cytosol. Western blot results indicated a significant reduction in MDR1 protein expression (approximately 50%) in treatment groups compared to control groups (FIGS. 15B & 15C). These results further demonstrated that the highest liver cancer cell inhibition of the RNA nanoparticles was not only a result of miR122 suppression of tumorigenic proteins such as ADAM10, but also a low effluxion of PTX drug from cell cytosol due to the down regulation of drug transporter MDR1.

Paclitaxel Release from RNA Nanoparticles

Figure 16A:
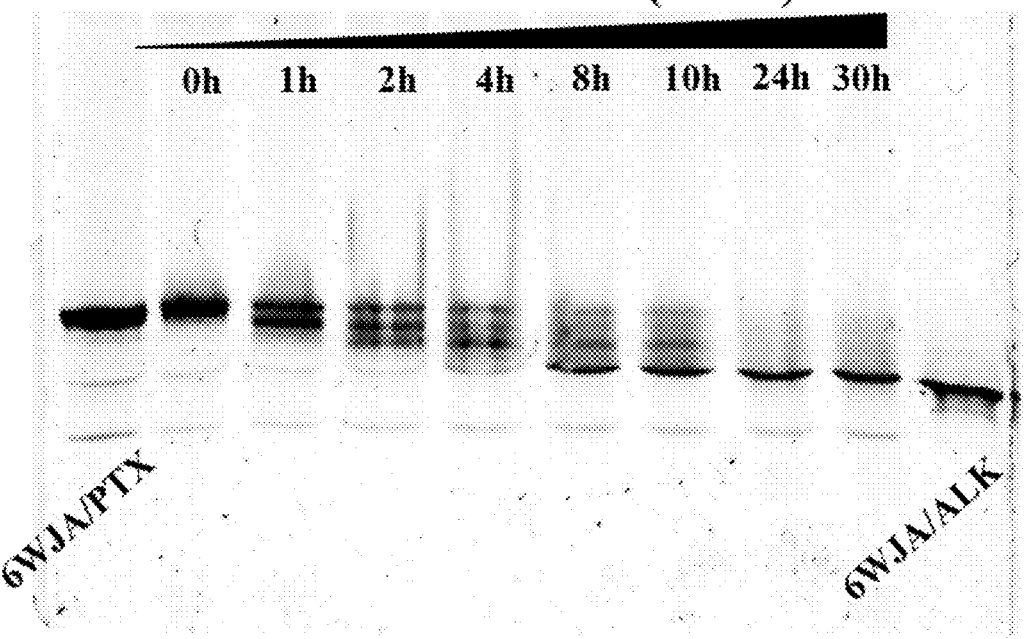
FIGS. 16A and 16B shows quantification of PTX release from RNA nanoparticles.

PTX conjugation to RNA as a prodrug was designed to improve its solubility and reduce its toxicity. Successful release of PTX from the RNA nanoparticle is vital to realize its anti-tumor effects. Therefore, the PTX release from PTX-RNA strands was first studied using 50% Fetal bovine serum (FBS), which is a well-known source of esterase enzyme, which cleaves ester bonds. The RNA-PTX strand was incubated with 50% FBS and the PTX was completely released from the RNA after 24 h of post incubation (FIG. 16A). The results indicated that the PTX was successfully released from the RNA strand due to ester bond cleavage by esterase.

Figure 16B:
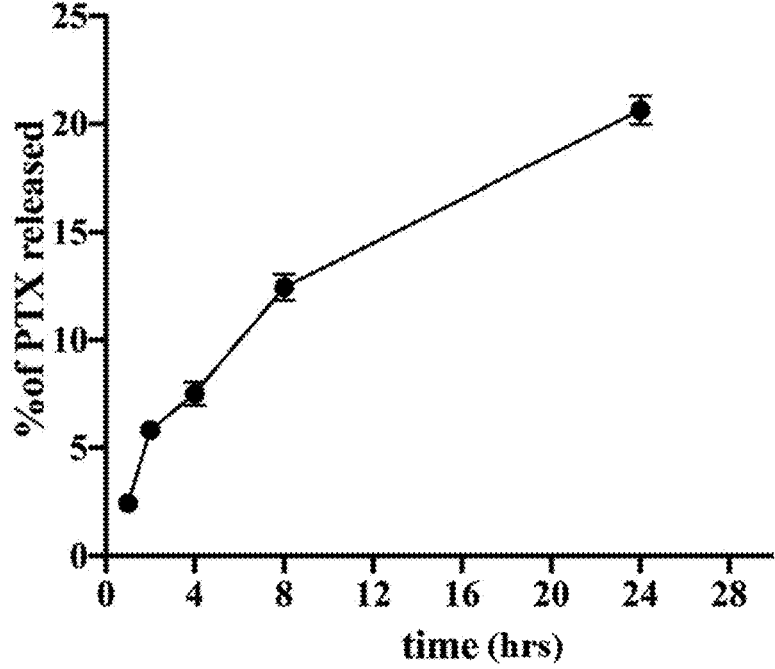

In addition, the release of PTX from 6WJ RNA nanoparticles was investigated through incubation with 50% FBS. The PTX released from the RNA nanoparticles was further assessed using LC/MS analysis. The results showed that majority of the PTX remains intact with RNA nanoparticles and only approximately 20% of PTX releases even after 24 h of incubation (FIG. 16B). The difference of PTX release from single stranded RNA and RNA nanoparticles may be attributed to the steric hindrance of the compact RNA nanoparticles to esterase enzymes. The results indicated that the PTX remain conjugated to RNA nanoparticles during systemic circulation, however, the PTX molecules might release from the RNA nanoparticles once they are metabolized into single stranded RNAs, which was also evident from both in vitro and in vivo cancer inhibition results.

Figure 17A:
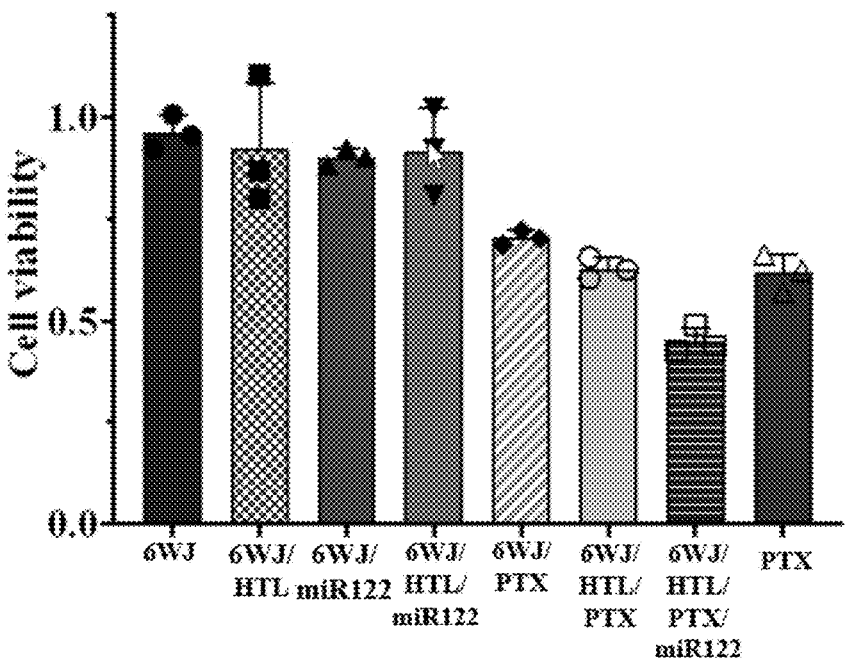
FIGS. 17A and 17B show in vitro assay for cancer cell inhibition and synergistic effect of 6WJ/HTL/miR122 and 6WJ/HTL/PTX nanoparticles.
Figure 17B:
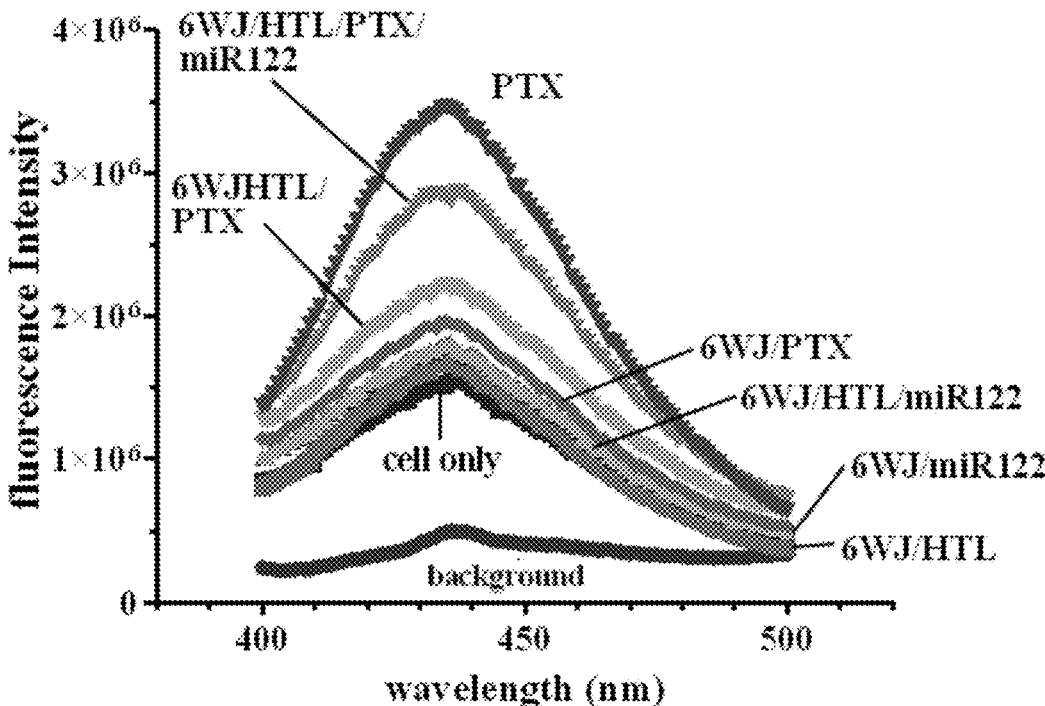
Figure 17C:
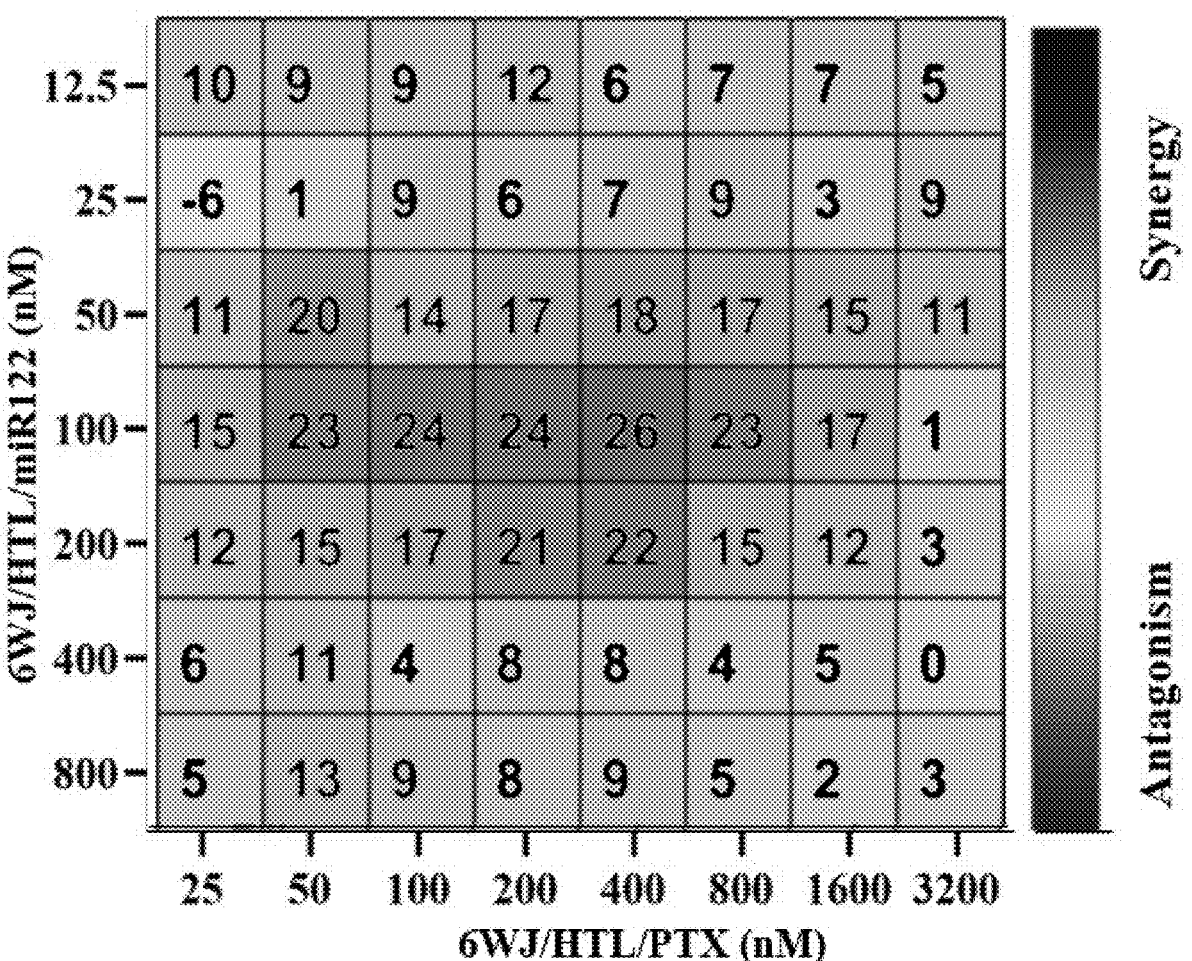
FIG. 17C shows synergetic cytotoxic effect between 6WJ/HTL/miR122 and 6WJ/HTL/PTX nanoparticles were assayed using HSA synergy model.

Evaluating Synergistic Cytotoxic Effect of the RNA Nanoparticles Harboring miR122 and PTX In Vitro The central theme of this novel study is that the targeted delivery of PTX and miR122 combination therapy by RNA nanoparticles results in enhanced toxicity to HCC cells due to their synergistic cytotoxic effect. To study the synergy between miR122 and PTX in cytotoxicity induction, an MTT cell viability assay was first performed. The RNA nanoparticles carrying miR122 and PTX showed the highest cell toxicity compared to the control groups harboring single treatment molecules (either PTX or miR122). Whereas 6WJ nanoparticles without treatment groups did not show any cancer cell inhibition effects, indicating the safety of RNA nanoparticles (FIG. 17A). A Caspase-3 activity assay was also used to further demonstrate the synergy between miR122 and PTX. The results showed that the treatment group with nanoparticles harboring both miR122 and PTX exhibited the highest apoptotic cell population compared to control groups using single treatments (FIG. 17B). Cell viability was used as an indicator to quantify the correlation of synergy between miR122 and PTX using Highest Single Agent (HSA) synergy modeling. The data was processed and quantified using Combenefit software to obtain the HSA synergy score between miR122 and PTX (FIG. 17C). In the matrix, the blue color at the middle of each drug concentration indicated the existing synergistic effect. The number represented the co-efficiency of synergy. The highest synergy between miR122 and PTX in cytotoxic induction was observed at 0.8 µM for miR122 and 3.2 µM for PTX. $IC_{50}$ was determined to be around 460 nM.

Figure 18A:
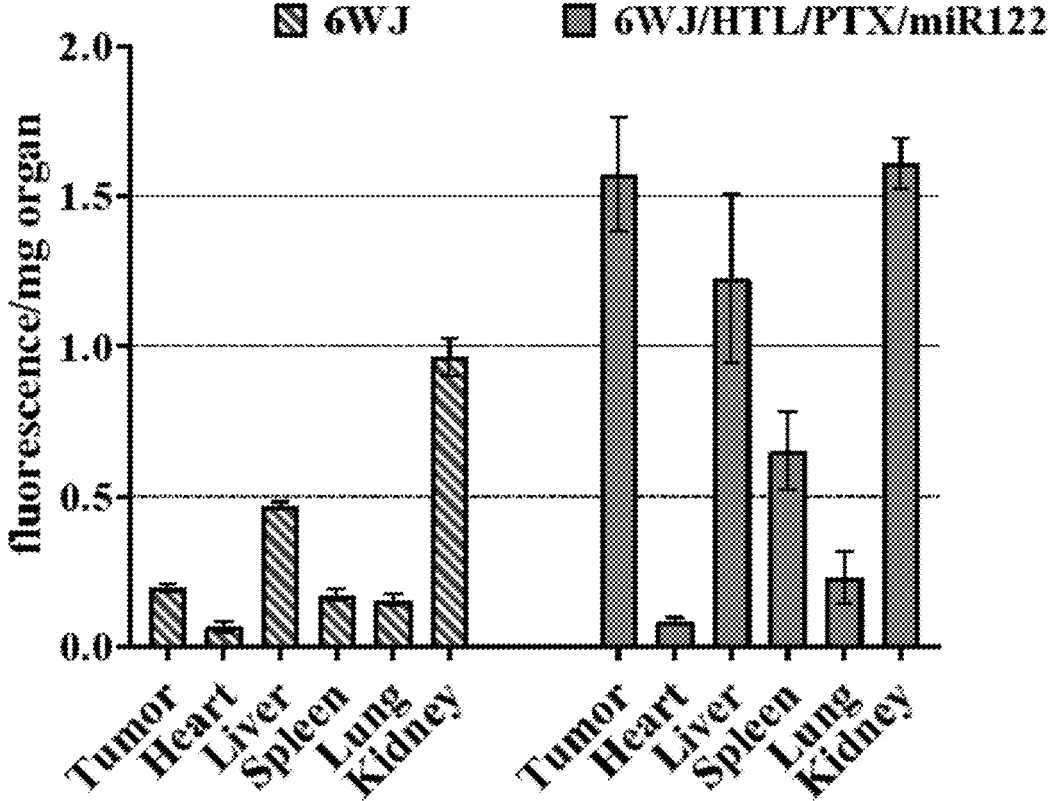
FIGS. 18A to 18C show animal trials for liver cancer inhibition by 6WJ/HTL/PTX/miR122 nanoparticles.

In Vivo Biodistribution Assay to Assess Tumor Targeting Effect and Organ Biodistribution of RNA Nanoparticles The asialoglycoprotein receptor has been widely used as a liver-specific target for drug delivery in various liver diseases, which is also proven effective in clinical trial. To evaluate the RNA nanoparticles' capabilities for tumor targeting in vivo, the HTL conjugated RNA nanoparticles were administered to HepG2 tumor bearing xenografts through IV injection. The mice were euthanized 8 h post-injection and organs were collected and imaged. The results showed that most of the HTL conjugated nanoparticles strongly accumulated in tumor, however, a slight accumulation in liver and kidney was also observed as the organs mainly function as drug filters. Mass normalized quantitative analysis of the organ images further indicated the higher tumor uptake ratio of 6WJ/HTL/PTX/miR122 compared to the negative control 6WJ (FIG. 18A). The biodistribution results proved that the hepatocyte targeting ligands could guide the RNA nanoparticles to tumor site and benefit the targeted drug delivery.

Figure 18B:
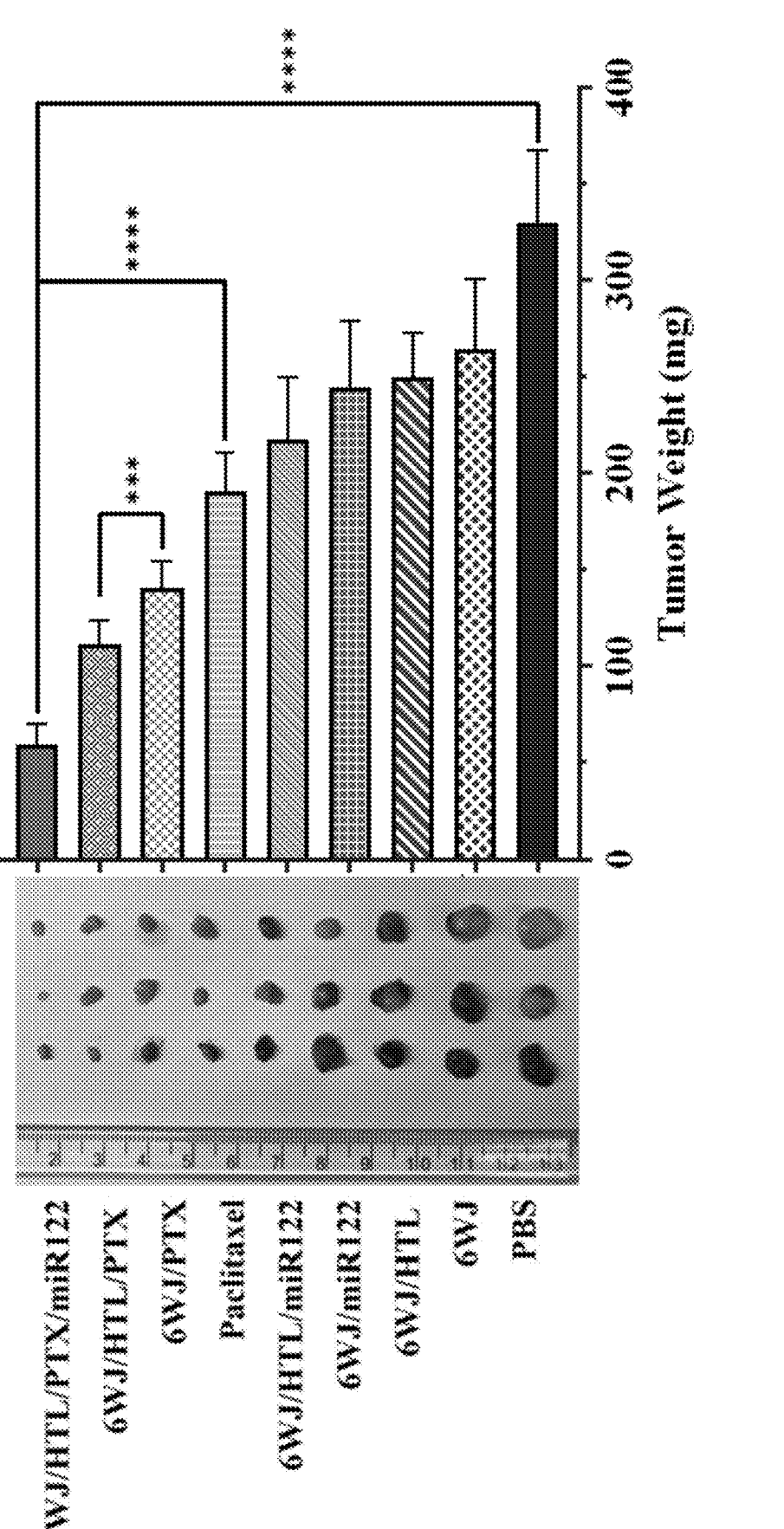
Figure 18C:

Therapeutic Efficacy of RNA Nanoparticles Carrying miR122 and PTX in Animal Trials After confirming the role of miR122 on the synergistic effect in combination with PTX in vitro, the therapeutic effect of the RNA nanoparticles was evaluated using HCC tumor bearing mice xenograft model. The RNA nanoparticles alongside controls were intravenously injected into mice at the clinically used dosage equivalent to 5 mg/kg (PTX dose per mouse weight) every 3 days for a total of 6 doses. Among all treatment groups, the mice administered with RNA nanoparticles harboring the combination therapy along with targeting ligands exhibited the highest tumor growth inhibition compared to other treatment groups carrying either PTX or miR122 with and without targeting ligands, which was evident from both tumor growth inhibition curves and reduced tumor weights (FIG. 18B-18D). Additionally, the RNA nanoparticles harboring targeting ligands showed better therapeutic results than without ligand groups, demonstrating the tumor targeting specificity. Importantly, clinically used PTX formulation (PTX mixed with Cremophor/EtOH) exhibited only a marginal tumor inhibitory effect. Together, the tumor inhibition results suggested that the highest therapeutic effect of the RNA nanoparticles attributed to i) EPR effect; ii) targeted drug delivery; iii) low drug effluxion from cytosol due to the down regulation of drug transporters by miR122; iv) synergistic effect between miR122 and PTX.

Induction of Pro-Inflammatory Factors by RNA Nanoparticles

Safety is another important concern for translational medicine. The immunogenicity of RNA nanoparticles has been proved to be tunable to produce either a minimal immune response as safe therapeutic vectors, or a strong immune activation for cancer immunotherapy with the incorporation of specific immune stimulation sequences. Here, the in vivo pro-inflammatory response after systemic injection of the nanoparticle formulation into the mice was further studied. The production of four pro-inflammatory cytokines were evaluated, including Tumor necrosis factor-$\alpha$ (TNF-$\alpha$), Interleukin 6 (IL6), Interferon-gamma (IFN$\gamma$), and Cytokine IL-12, upon RNA nanoparticle treatment in an immune competent mice model. ELISA assay indicated that intravenous (IV) injection of RNA nanoparticles at the dose of 5 mg/kg induced undetectable or negligible cytokines production (FIG. 19). In contrast, PTX formulated in Cremophor EL/EtOH induced elevated production of these immune response indicators. The in vivo pro-inflammatory results demonstrated the safety of the developed RNA nanoparticles.

Discussion

Liver tumor targeting RNA nanoparticles were constructed for the co-delivery of miR122 and PTX which increased the therapeutic efficacy against liver cancer through both passive EPR effect and active tumor targeting by tumor specific ligands. Hydrophobic PTX was conjugated to RNA as pro-drugs with improved solubility, lower toxicity, and higher therapeutic efficiency. Exogeneous delivery of miR122 to HCC successfully downregulates tumorigenic proteins as well as inhibits tumor migration, proliferation and metastasis. More importantly, miR122 could suppress the drug efflux transporters expression, such as P-glycoproteins, leading to the synergetic effect with PTX by overcoming the HCC drug resistance to PTX as well as sensitizing the HepG2 cells to PTX treatment. The in vivo results reveal the high tumor targeting specificity of the RNA nanoparticle formulation as well as the strong tumor growth inhibition efficiency, arising from the synergistic effect between miR122 and PTX, which is superior than commercially used PTX formulation (Cremphol/EtOH). Overall, these findings demonstrate that the multivalent targeted drug delivery using 6WJ motif has a high potential to treat liver cancer effectively.

Although tumor targeted delivery can increase the therapeutic efficacy, there are some concerns that nanoparticles may also deliver the anti-cancer drugs to non-target organs and tissues, resulting in undesirable side effects and toxicity. The multivalent RNA nanoparticle conjugated with miR122, PTX, and HTLs show undetectable immunogenicity and toxicity in mice xenograft. This safety profile is attributed to the unique properties of RNA nanotechnology: 1) Optimal size and elasticity of RNA nanoparticles; Rubber-like deformation property of RNA nanoparticles allows for squeezing through tumor vasculature to improve the EPR effect. RNA structures with the size of 10-20 nm avoid reticuloendothelial system (RES) clearance in the liver, spleen, lung, and bone marrow, which induce nonspecific uptake by innate immune cells such as macrophages. The unique size and elasticity of RNA carriers facilitate passing through direct glomerular filtration where larger molecules cannot be eliminated. The rapid excretion of RNA nanoparticles by direct kidney filtration thus avoiding retention in healthy organs and tissues. 2) Increased solubility of hydrophobic drugs conjugated to RNA prevents the nonspecific binding and accumulation into normal cells and eventual toxicity. Solubilizing the drugs also enhances the drug bioavailability and reduces the injection dose, further lowering the potential side effects. 3) High thermodynamic stability and chemical stability of RNA nanoparticles keep RNA structures intact in vivo, avoiding nonspecific release of toxic drugs. MiRNAs conjugated to RNA nanoparticles facilitate high stability, thus avoiding enzyme degradation and immunotoxicity.

Combining these advantages, it was anticipate that the developed RNA nanotechnology platform with targeting ability will find extensive use in delivering various drugs/imaging markers to various cancer types as a safe delivery platform that enable new advances in the fields of cancer and biomedical applications.

Conclusions

The newly developed 6WJ RNA nanoparticles with defined size allows us to conjugate three liver targeting ligands, one copy of miR122 and 24-copies of PTX drug. The miR122 downregulated the tumor oncogenic factor and the drug efflux transporter, which in turn, inhibited the expulsion of the delivered drugs and sensitized tumor cells for PTX. The increased therapeutic efficacy in mice xenograft model is a combined effect of the multivalent RNA nanoparticles. The rubber-like property of the multivalent RNA nanoparticles enhances their tumor vascularization. The specific tumor cell targeting and entry effect is attributed to the three copies of the liver cell targeting ligands. The gene silencing and tumor suppression efficiency are attributed to the miR122 that silence the P-glycoproteins, which is a drug efflux transporter that leads to HCC resistance for drugs such as PTX. In vivo studies on mice xenografts revealed that the RNA nanoparticles predominantly accumulate in HCC tumor and efficiently inhibited the tumor growth after 22 days of intravenous (IV) administration. Most importantly, the nanoparticles are safe to use because of their tumor specificity, non-immunogenicity, fast renal clearance, undetectable liver accumulation, and fast tumor homing. Thus, the multivalent 6WJ nanoparticles are rapidly becoming a promising therapeutic for the treatment of the currently incurable liver cancer.

Methods and Experimental

Design and Construction of 6WJ RNA Nanoparticles

Multifunctional RNA nanoparticles were constructed using a bottom-up self-assembly approach. The 6WJ/HTL/PTX/miR122 contains seven RNA fragments (FIG. 13A) harboring ASGP-R targeting ligands, 24 copies of PTX and miR122. The controls include RNA nanoparticles without a targeting ligand (denoted as 6WJ/PTX/miR122); without a therapeutic module (denoted as 6WJ/HTL), or without therapeutic and targeting modules (denoted as 6WJ).

RNA strands were synthesized chemically using solid-phase synthesis. 2'-Fluoro (2'-F) modified cytosine (2'F-C) and uracil (2'F-U) nucleotides are incorporated in the RNA sequences to improve the RNA nanoparticle's thermal stability and nuclease resistance. RNA sequences can be found in Supplementary information.

6WJ Nanoparticle Assembly

The 6WJ nanoparticles are synthesized by a bottom-up self-assembly of the single-stranded RNA fragments. The RNA strands were mixed at equal molar concentrations in an annealing Buffer (1×PBS), and heated to 95° C. for 5 min, then slowly cooled to 4° C. over 45 min. Self-assembly of the RNA nanoparticles was verified on a 2% agarose gel running in 1×TAE (89 mM Tris-Acetate, 2 mM EDTA) buffer and imaged using Typhoon FLA 7000.

Melting Profile Determination Using TGGE Method

The self-assembled nanoparticles were loaded on to 10% native PAGE gel and ran for 15 mins at 140 V prior to TGGE in 1×TBE buffer (100 mM Tris-Borate, 1 mM EDTA). After running the RNA nanoparticle into the gel matrix, the gel was subjected to TGGE by increasing the temperature in a gradient manner perpendicular to the electrophoretic force from 30 to 80° C. The gel run in 1×TBS at 100 V for 45 min then, imaged using Typhoon FLA 7000.

Annealing Profile Determined Using Thermal Cycler

Pre-assembled RNA nanoparticles were added to a 96-well plate with a final concentration of 2.5 µM or 1 µM, respectively. Then, the RNA nanoparticles were mixed with SYBR Green II (as a reporter dye at a final concentration of 20×) at 2.5 µM and 1.0 µM concentrations. All samples were independently completed in triplicate. The RNA nanoparticle samples were heated to 95° C. for 5 min then slowly cooled to 20° C. at a rate of 0.11° C./s using a Roche Lightcycler 480 machine. The RNA nanoparticle formation was monitored by measuring fluorescence levels at 480.0 nm excitation and plotted against temperature and the $T_a$ values were determined as the temperatures at which 50% of maximum SYBR green II fluorescence was detected.

Size Measurement Using DLS

The apparent hydrodynamic sizes for the assembled RNA nanoparticles (6WJ, 6WJ/HTL/PTX, and 6WJ/HTL/PTX/miR122) were measured at 25° C. by Zetasizer nano-ZS machine. The data was obtained from three independent measurements.

PTX Release Assay

The PTX release profile from the 6WJ/PTX/HTL/miR122 nanoparticle was studied by incubating them in 50% Fetal Bovine Serum (FBS) at 37° C. at a final concentration of 2 µM. The single strand PTX-RNA was incubated in FBS at different time intervals (0, 0.5, 1, 2, 4, 8, 12, 24, and 30 h), then, 10 µL of each sample was collected and subjected for a gel shift assay. The samples were run on a 16% urea PAGE gel in 1×TBE at 160 V for 100 min and then imaged by Typhoon FLA 7000. In the study of PTX release from assembled RNA nanoparticles, the RNA nanoparticles were incubated in FBS at different time intervals (0, 0.5, 1, 2, 4, 8, 12 h). Then, 50 µL of each sample was collected and the released free PTX was extracted with 200µ MTBE. After vortex, 200µ MTBE was collected and dried by a speed vacuum. The PTX was resuspend in MeOH and subject to LC/MS.

Cell Culture

Human hepatocellular carcinoma cells (HepG2) were obtained from the ATCC. Cells were grown and cultured in DMEM medium (ThermoFisher Scientific) containing 15% (v/v) Fetal Bovine Serum (FBS) in humidified air environment containing 5% $CO_2$.

Confocal Microscopy Imaging

HepG2 cells were seeded on glass coverslips and cultured at 37° C. incubator overnight. Cells were treated with RNA nanoparticles conjugated with an Alexa 647 marker at 100 nM final concentration for 4 h at 37° C. After incubation, cells were washed twice with cold PBS buffer, then fixed with 4% formaldehyde. Cells were then treated with 0.1% Triton X-100 (Sigma-Aldrich) in PBS buffer for 5 min then treated with cytoskeleton staining dye Alexa Fluor 488 phalloidin (ThermoFisher Scientific) for 30 min at room temperature. After rinsing with PBS buffer, the cells were stained by DAPI for cell nucleus staining and mounted with ProLong® Gold Antifade Reagent (Life Technologies Corp., Carlsbad, CA. The slides were assayed on Olympus FV3000 confocal microscope (Olympus Corporation, Tokyo, Japan).

In Vitro Cytotoxicity Assay

A CellTiter 96 Non-Radioactive Cell Proliferation Assay (Promega) was used for cell cytotoxicity study, following manufacturer instructions. Briefly, $5 \times 10^3$ HepG2 cells were seeded on a 96-well plate overnight. Triplicate wells were treated with RNA nanoparticles and free PTX were added at 400 nM. After incubation at 37° C. for 48 h in a 5% humidified $CO_2$ environment, 15µ of MTT Dye was aliquot to each well. The cells were incubated at 37° C. for 4 h following 50 µL of Solubilization Solution/Stop Mix was added to each well. The plate was incubated in the dark overnight on a shaker at room temperature to a uniformly colored solution and subjected to absorbance measurement at 570 nm by Synergy 4 microplate reader (Bio-Tek).

In Vitro Apoptosis Assay

Caspase 3 Apoptosis Detection Kit (BD Pharmingen) was used for cell apoptosis following manufacturer instructions. HepG2 cells were seeded in a 24-well plate overnight and treated with 400 nM of the 6WJ/HTL/PTX/miR122 nanoparticles and its controls for another 24 h at 37° C. Then, the cells were lysed using the cold cell lysis buffer, and 25 µL cell lysate of each treatment group was transferred to 0.6 ml tube, 2 µL of reconstituted Ac-DEVD-AMC diluted in 80 µL of HEPES buffer was added to each tube and incubated at 37° C. for 1 h. The fluorescent intensity of caspase-3-AMC substrate was measured by fluorometer at 400-500 nm window with an excitation of 380 nm.

HSA Synergy Modeling

Cell viability was studied following MTT protocol in cytotoxicity assay. The result was presented by Prism 8.0 (Graph Pad). The viability result was entered into HSA synergy modeling by Combenefit and plotted by Prism 8.0.

qRT-PCR Assay to Study Downstream Gene Expression qRT-PCR Assay was performed following the procedure (Life Technologies) to study the ADAM10 mRNA expression. HepG2 cells were cultured with treatment groups at 400 nM final concentration for 48 h at 37° C. before the total RNA was extracted by TRIzol reagent (Life Technologies). Next, the cDNA strand was reverse transcript from total RNA (1 µg) using SuperScript III First-Strand Synthesis System (Life Technologies). qRT-PCR was performed in a final 20 µL volume using Taqman Universal PCR Master mix, primers and probe, and cDNA. The primer and probe for human ADAM10 and GADPH (housekeeping gene) were purchased from Life Technologies. PCR was performed on StepOnePlus systems (Applied Biosystem). The data were analyzed by the ΔΔCT method.

Western Blot Assay to Study Downstream Gene Expression

Western blot assay was used to investigate the ADAM10 and MDR1 protein expression. The HepG2 cells were cultured on a 24-well plate overnight at 37° C. Then, cells were treated with 400 nM of the RNA nanoparticles following incubation for 72 h, and were lysed in RIPA buffer with protease inhibitor. Total protein concentration was quantified by BCA Protein Assay Kit. A total of 10 μg of protein was loaded into a 10% SDS PAGE. The gel was transferred to polyvinylidene fluoride membrane and followed by blocking in 5% fat-free milk on shaker at room temperature for 2 h. The membrane was then stained with primary antibody (rabbit-ADAM 10: 1:1000; mouse-GADPH: 1:10 000) at 4° C. overnight and washed with TBST buffer three times for 5 min each time. The membrane was then stained with secondary antibody (goat pAb to rabbit IgG and goat pAb to mouse IgG: 1:10 000) at room temperature for 1 h and washed with TBST buffer three times for a total of 15 min. Membranes were then incubated with ECL substrate, exposed to Amersham HYPERFILM together, and processed with a Series 2000A Processor film developer.

Subcutaneous Tumor Xenograft Animal Model

All animal procedures were housed and operation was performed in accordance with the subcommittee on Research Animal Care of The Ohio State University guidelines approved by the Institutional Review Board. To generate the Hepatocellular carcinoma xenograft model, female athymic nu/nu mice, 3-4 weeks old purchased from Charles River Laboratories were subcutaneously injected $2 \times 10^6$ HepG2 cells/site resuspended in sterile PBS into the mammary fat pads of nude mice.

In Vivo Biodistribution Study

Alexa 647 labeled 6WJ nanoparticles (100 μl, 20 μM) were administered by IV injection into HepG2 tumor bearing mouse xenograft. PBS treatment was used as background control. The mice were euthanized 8 h post-injection by the inhalation of $CO_2$ followed by cervical dislocation, and major organs (heart, liver, spleen, lungs, kidneys, tumor) were harvested and subjected to imaging by IVIS (XMRS) with excitation at 640 nm and emission at 680 nm. Fluorescence imaging was analyzed and quantified by Living Imaging (Perkin Elmer).

In Vivo Tumor Inhibition by RNA Nanoparticles

HepG2 tumor bearing mouse xenograft were randomly divided into nine groups (n=5 each group). Samples were administrated by IV injection in a total of 6 doses (5 mg/kg, PTX/body weight) every 3 days for 21 days. Tumor volume was monitored every day by caliper, calculated as (length× width$^2$)/2, and mice weight was monitored every day. On day 21, the mice were sacrificed, and tumors were extracted. Data were statistically analyzed by unpaired t-test and presented as mean±SD; *p<0.005, **p<0.0005.

In Vivo Cytokines Induction Evaluation

CD-1 mice (4-5 weeks old) were purchased from Charles River Laboratories. RNA nanoparticles and controls were administered into mice with three biological replicates via IV injection at 5 mg/kg (PTX/body weight). Three hours post-injection, blood samples were harvested from mice by cardiac puncture and serum was separated by centrifugation at 12,800×g for 10 min. Concentrations of cytokine TNF-α, IL-6, IL-12 and IFN-γ in serum supernatant were examined in triplicates using Mouse ELISA MAX Deluxe sets (BioLegend), following manufacturer provided protocols.

Statistics

Each experiment for each tested sample was repeated at least three times independently and the results were presented as mean±standard deviation (S.D.). Statistical differences were evaluated using unpaired t-test with GraphPad software, and p<0.05 was considered statistically significant.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition for treating hepatocellular carcinoma (HCC), comprising an RNA nanostructure conjugated to
   a) one to three hepatocyte targeting ligands,
   b) a plurality of paclitaxel prodrugs, and
   c) a therapeutic miR122 oligonucleotide that suppresses or silences a drug efflux transporter,
   wherein at least one of the one to three hepatocyte targeting ligands comprises a 4-(((2R,3R,4R,5R,6R)-3-acetamido-4,5-dihydroxy-6-(hydroxymethyl)tetrahydro-2H-pyran-2-yl)oxy)-N-(6-(4,4-bis(hydroxymethyl)piperidin-1-yl)-6-oxohexyl)butanamide molecule.

2. The composition of claim 1, wherein the composition three parallel 4-(((2R,3R,4R,5R,6R)-3-acetamido-4,5-dihydroxy-6-(hydroxymethyl)tetrahydro-2H-pyran-2-yl)oxy)-N-(6-(4,4-bis(hydroxymethyl)piperidin-1-yl)-6-oxohexyl)butanamide molecules.

3. The composition of claim 1, comprising about 24 paclitaxel prodrug molecules.

4. The composition of claim 1, wherein the RNA nanoparticle comprises three to six self-assembled synthetic RNA oligonucleotides.

5. The composition of claim 4, wherein the three to six synthetic RNA oligonucleotides form a central core domain and at three to six double-stranded arms arranged around the core domain and extending away from the central core domain.

6. The composition of claim 5, wherein the one to three hepatocyte targeting ligands are conjugated to a first double-stranded arm.

7. The composition of claim 3, wherein the at least three hepatocyte targeting ligands are all conjugated to the first double-stranded arm.

8. The composition of claim 4, wherein a second double stranded arm comprises a sequence portion that is bound to the therapeutic miR122 oligonucleotide by complementary or partial complementary binding.

9. The composition of claim 4, wherein the paclitaxel prodrugs are conjugated to one or more of the double-stranded arms by click chemistry.

10. A method of treating a liver cancer in a subject, comprising administering to the subject a therapeutically effective amount of the composition of claim 1.

11. The composition of claim 1, wherein the one to three hepatocyte targeting ligands are connected to one another via a phosphate backbone.

* * * * *